US005789408A

United States Patent [19]
Kleinman et al.

[11] Patent Number: 5,789,408
[45] Date of Patent: *Aug. 4, 1998

[54] ANTIVIRAL THIAZOLES

[75] Inventors: Edward Fox Kleinman, Pawcatuck; Hiroko Masamune, Noank; Vinod Dipak Parikh, Mystic, all of Conn.

[73] Assignee: Pfizer Inc., New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 586,832

[22] PCT Filed: May 19, 1994

[86] PCT No.: PCT/IB94/00113

§ 371 Date: Jan. 11, 1996

§ 102(e) Date: Jan. 11, 1996

[87] PCT Pub. No.: WO95/05378

PCT Pub. Date: Feb. 23, 1995

Related U.S. Application Data

[63] Continuation of Ser. No. 109,757, Aug. 19, 1993, abandoned.

[51] Int. Cl.$^6$ .............. A61K 31/425; C07D 277/30; C07D 213/60; C07D 215/16
[52] U.S. Cl. .............. 514/252; 514/256; 514/259; 514/249; 514/248; 514/307; 514/314; 514/342; 514/367; 514/369; 548/186; 544/235; 544/238; 544/284; 544/298; 544/333; 544/405; 544/354; 546/269.1; 546/152; 546/153; 546/141; 546/148

[58] Field of Search .............. 546/269.7, 152, 546/153, 141, 148; 544/235, 238, 284, 298, 333, 405, 354; 548/186; 514/252, 256, 259, 249, 248, 307, 314, 342, 367, 369

[56] References Cited

U.S. PATENT DOCUMENTS

| | | | |
|---|---|---|---|
| 4,701,452 | 10/1987 | Limbert et al. | 514/206 |
| 4,738,972 | 4/1988 | Eggler | 514/314 |
| 4,762,848 | 8/1988 | Scheunemann et al. | 514/369 |
| 4,963,577 | 10/1990 | Schorlemmer et al. | 514/369 |
| 5,114,939 | 5/1992 | Dreikorn | 514/248 |
| 5,294,622 | 3/1994 | Dreikorn | 514/311 |

FOREIGN PATENT DOCUMENTS

| | | |
|---|---|---|
| 0194571 | 9/1986 | European Pat. Off. . |
| 0194572 | 9/1986 | European Pat. Off. . |
| 0342565 | 11/1989 | European Pat. Off. . |

*Primary Examiner*—Bernard Dentz
*Assistant Examiner*—D. Margaret M. Mach
*Attorney, Agent, or Firm*—Peter C. Richardson; Gregg C. Benson; Robert T. Ronau

[57] ABSTRACT

Compounds of formula (I) are active antiviral compounds useful in the treatment of viral infections in mammals. The compounds of the invention are readily prepared by reaction of a suitable 2-thiothiazole derivative with an appropriate Het-$(CH_2)_n$-halide.

12 Claims, No Drawings

ANTIVIRAL THIAZOLES

CROSS-REFERENCE TO RELATED APPLICATIONS

This application is the national stage under 35 U.S.C. §371 of International Application no. PCT/IB94/00113, filed May 19, 1994 which is a continuation of U.S. application Ser. No. 08/109,757, filed Aug. 19, 1993, now abandoned.

BACKGROUND OF THE INVENTION

This invention relates to new chemical compounds which have value in the area of medical science. More particularly, this invention relates to new chemical compounds which are of value for the administration to a mammalian subject, particularly man, for the treatment of viral infectious diseases. The new chemical compounds of this invention having utility in treating viral infectious diseases are thiazole derivatives of the general formula (I),

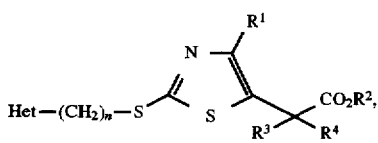

wherein Het, n, $R^1$, $R^2$, $R^3$ and $R^4$ are as defined hereinbelow.

Notwithstanding the success which has been achieved in the area of antibiotic therapy, very little progress has been made in efforts to develop broad-spectrum anti-viral agents. A major problem with antiviral agents historically has been the presence of toxic side effects. Most currently known anti-viral agents have also been shown to down-regulate various immune parameters such as lymphocyte function. Accordingly, there is a clear need for a safe pharmacological agent with broad spectrum activity against viral infections.

Activated cytotoxic T cells are important in effecting the clearance of virally infected cells. An agent that can directly or indirectly increase cytotoxic T cell function should therefore enhance the clearance of virally infected cells and decrease the severity and duration of viral infection. In addition, such an agent may serve as an adjuvant for viral vaccines. Since most viral infections can be cleared by the activation of cytotoxic T cells, an agent that increases cytotoxic T cell function will have broad spectrum antiviral activity.

These new viral infectious disease treating agents are related to the medicinal agent known as tiprotimod, which is described in detail in U.S. Pat. Nos. 4,762,848 and 4,963,577. It has been reported that tiprotimod, the compound of formula (II), has a therapeutic effect on viral infectious diseases without causing adverse toxic side effects. Schorlemmer et al., U.S. Pat. No. 4,963,577.

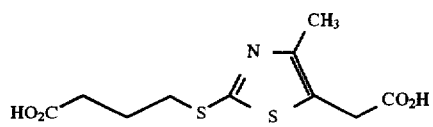

SUMMARY OF THE INVENTION

This invention provides compounds of the formula

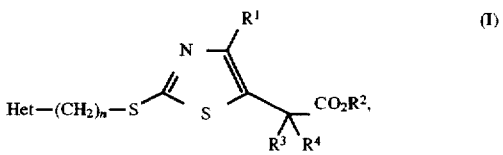

or a pharmaceutically acceptable salt thereof, wherein: $R^1$ is —$(C_1-C_4)$alkyl; $R^2$ is H, —$(C_1-C_4)$alkyl, —$(C_3-C_7)$cycloalkyl or benzyl; $R^3$ and $R^4$ are taken separately and are independently H or —$(C_1-C_4)$alkyl, or $R^3$ and $R^4$ are taken together to form a five- or six-membered carbocycle; n is 0, 1 or 2; Het is

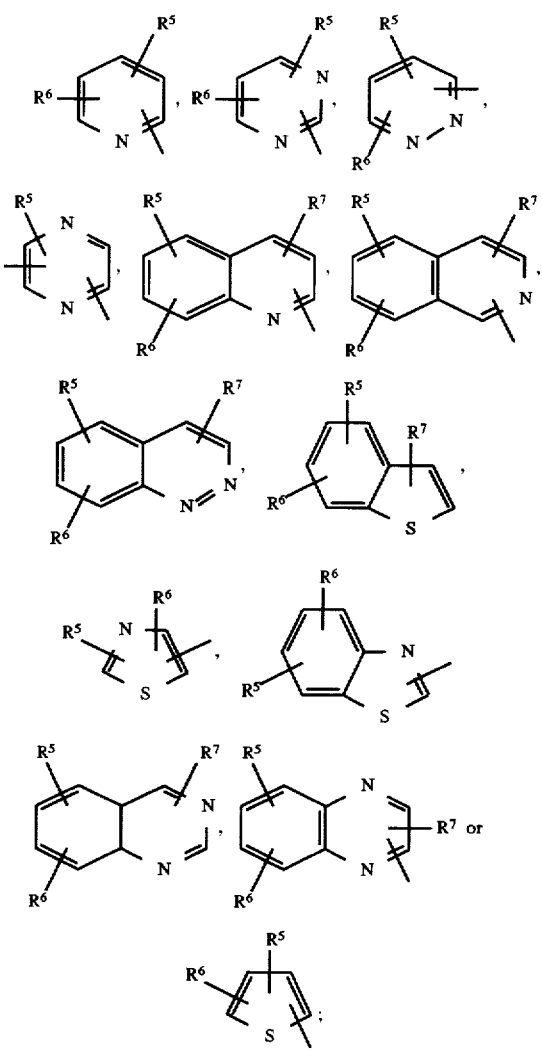

$R^5$ is H, methyl, —$CF_3$, —$CHF_2$, —$CH_2F$, chloro, fluoro, bromo, nitro, hydroxy, —$(C_1-C_4)$alkoxy, mercapto, —$(C_1-C_4)$alkylthio, —$(CH_2)_pCO_2R^8$, amino, —$(C_1-C_4)$alkylamino or $(C_1-C_4)$dialkylamino; $R^6$ and $R^7$ are independently H, methyl, —$CF_3$, —$CH_2F$, —$CHF_2$, chloro, fluoro, bromo, nitro, hydroxy, —$(C_1-C_4)$alkoxy, mercapto, —$(C_1-C_4)$alkylthio, amino, —$(C_1-C_4)$alkylamino or —$(C_1-C_4)$dialkylamino; $R^8$ is H, —$(C_1-C_4)$alkyl, —$(C_3-C_7)$cycloalkyl or benzyl; and p is 0, 1 or 2; provided that when n is 0 and $R^3$ and $R^4$ are H, Het is not

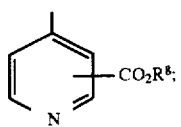

and further provided that when Het is

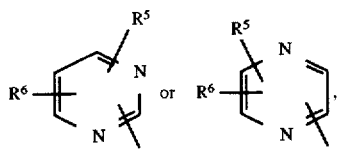

$R^5$ and $R^6$ are each not chloro, fluoro or bromo.

Preferred compounds of this invention are the compounds of formula (I) wherein Het is

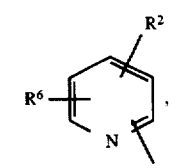

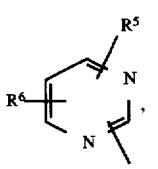

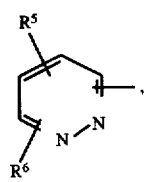

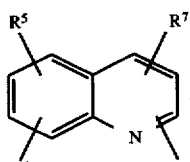

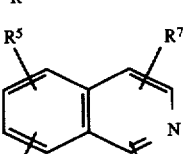

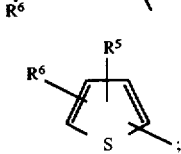

$R^3$, $R^4$ and $R^7$ are each H; $R^2$ is H, methyl or ethyl; n is 0; $R^5$ is H, —$CO_2R^8$, methyl, —$CH_2CO_2R^8$, ($C_1$–$C_4$) alkylthio, methoxy or trifluoromethyl; and $R^1$, $R^6$ and $R^8$ are as defined above.

More preferred compounds within this group are the compounds of the preferred group wherein Het is

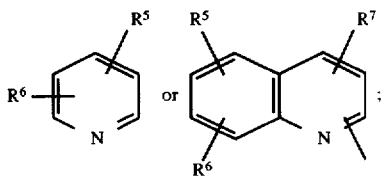

$R^5$ is —$CO_2R^8$; $R^6$ is H, methyl or methoxy; and $R^1$, $R^2$, $R^3$, $R^4$, $R^7$ and n are as defined in the preferred group.

The most preferred compounds of formula (I) of this invention are the following compounds: 4-((5-carboxymethyl-4-methyl-2-thiazolyl)thio)-8-methoxyquinoline-2-carboxylic acid; 2-((5-(2-ethoxy-2-oxoethyl)-4-methyl-2-thiazolyl)thio)-4-methyl-3-pyridine carboxylic acid; and 2-((5-carboxymethyl-4-methyl-2-thiazolyl)thio)-6-pyridine-carboxylic acid ethyl ester.

Also preferred compounds of formula (I) of this invention are the compounds of formula (I) wherein Het is

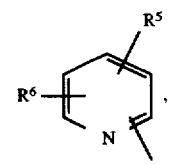

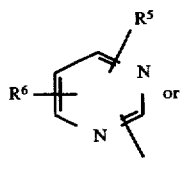

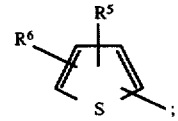

and $R^5$ is —$CO_2R^8$, —OH or ($C_1$–$C_4$)alkyl; n is 1; and $R^1$, $R^2$, $R^3$, $R^4$, and $R^6$ are as defined above.

This invention further provides the intermediate N-oxide compounds of formula (III),

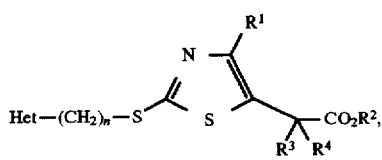

(III)

wherein $R^1$ is H or ($C_1$–$C_4$)alkyl; $R^2$ is H, ($C_1$–$C_4$)alkyl, ($C_3$–$C_7$)cycloalkyl or benzyl; $R^3$ and $R^4$ are taken separately and are independently H or ($C_1$–$C_4$)alkyl, or $R^3$ and $R^4$ are taken together to form a five- or six-membered carbocycle; n is 0, 1 or 2; Het is

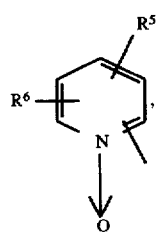

-continued

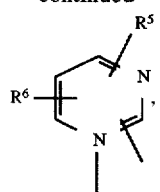

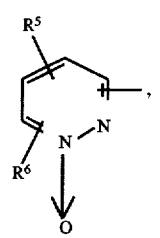

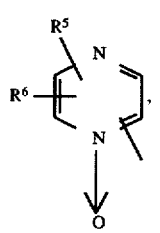

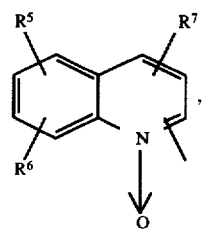

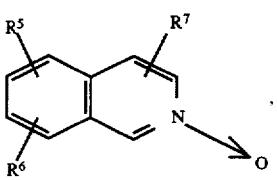

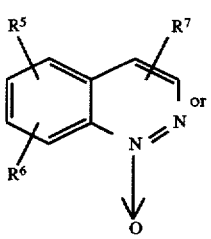

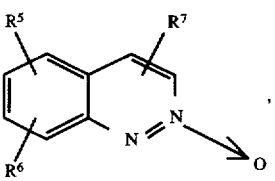

-continued

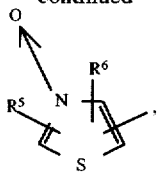

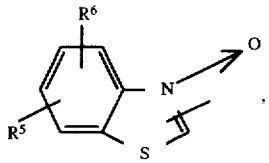

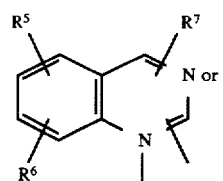

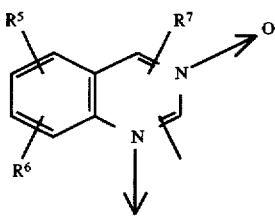

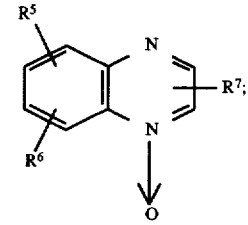

$R^5$ is independently H, methyl, —$CF_3$, —$CHF_2$, —$CH_2F$, nitro, hydroxy, ($C_1$–$C_4$)alkoxy, mercapto, ($C_1$–$C_4$)alkylthio, $(CH_2)_pCO_2R^8$, amino, ($C_1$–$C_4$)alkylamino, ($C_1$–$C_4$) dialkylamino, fluoro, chloro, or bromo; $R^6$ and $R^7$ are independently H, methyl, $CF_3$, $CH_2F$, $CHF_2$, chloro, fluoro, bromo, nitro, hydroxy, ($C_1$–$C_4$)alkoxy, mercapto, ($C_1$–$C_4$) alkylthio, amino, ($C_1$–$C_4$)alkylamino or ($C_1$–$C_4$) dialkylamino; $R^8$ is H, ($C_1$–$C_4$)alkyl, ($C_3$–$C_7$)cycloalkyl or benzyl; and p is 0, 1 or 2; provided that when n is 0 and $R^3$ and $R^4$ are H, Het is not

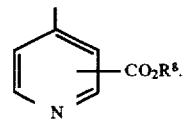

The invention further provides a method for treating a viral infection in a mammal comprising administering to said mammal an effective amount of a compound according to formula (I) or a pharmaceutical composition thereof.

The invention still further provides a pharmaceutical composition for use in a mammal suffering from a viral infection which comprises an effective amount of a compound according to formula (I) and a pharmaceutically acceptable carrier or diluent.

DETAILED DESCRIPTION

The compounds of this invention are readily prepared. Thus, when $R^2$ and $R^8$ are both H, and the compound of formula (I) thus has two free carboxylic acid groups, the compound of formula (I) wherein $R^2$ and $R^8$ are hydrogen (the diacid) is prepared by reacting a compound of formula (I) wherein $R^2$ and $R^8$ are each independently ($C_1$–$C_4$)alkyl, ($C_3$–$C_7$)cycloalkyl or benzyl under aqueous base hydrolysis conditions well known to one skilled in the art. Thus the compound of formula (I) wherein $R^2$ and $R^8$ are each independently ($C_1$–$C_4$)alkyl, ($C_3$–$C_7$)cycloalkyl or benzyl (the diester) are dissolved in a mixture of water and an alcoholic solvent such as methanol, ethanol or propanol and is cooled to a temperature of about −20° C. to about 10° C. The reaction mixture is treated with an excess of an aqueous base and stirred for about 30 minutes to about 24 hours. Aqueous bases which are useful for this reaction include potassium carbonate, sodium and potassium hydroxide. The preferred reaction conditions comprise reacting the diester with sodium hydroxide in a solvent system of methanol and water at about 0° C. When the reaction is complete the dicarboxylic acid compound of formula (I) wherein $R^2$ and $R^8$ are both hydrogen is isolated via methods well known to one of skill in the art.

Alternatively, the compounds of formula (I) wherein $R^2$ and $R^8$ are both hydrogen (the diacid) are prepared by reacting a compound of formula (I) wherein $R^2$ is hydrogen and $R^8$ is ($C_1$–$C_4$)alkyl or ($C_3$–$C_7$)cycloalkyl or a compound of formula (I) wherein $R^2$ is ($C_1$–$C_4$)alkyl or ($C_3$–$C_7$) cycloalkyl and $R^8$ is hydrogen under the same aqueous base reaction conditions described in the foregoing paragraph. Sodium hydroxide is the preferred alkaline hydroxide and methanol/water is the preferred solvent system, though it will be recognized by one skilled in the art that with some substrates other bases and/or other alcoholic solvents will be acceptable.

Also embraced within the scope of this invention are the compounds of formula (I) wherein $R^2$ is hydrogen and $R^5$ is neither a carboxylic acid nor a carboxylic acid ester, thus forming the monocarboxylic acid compounds of formula (I) of the invention. The monocarboxylic acid compounds of formula (I) are prepared utilizing the same aqueous base hydrolysis reaction conditions described hereinabove. The preferred base is sodium hydroxide and the preferred solvent system is methanol/water.

To prepare the mono ester compounds of formula (I) of this invention wherein $R^2$ is ($C_1$–$C_4$)alkyl or ($C_3$–$C_7$) cycloalkyl and $R^8$ is hydrogen, a compound of formula (I) wherein $R^2$ is ($C_1$–$C_4$)alkyl or ($C_3$–$C_7$)cycloalkyl and $R^8$ is benzyl is reacted under acid hydrolysis conditions. Typically a compound of formula (I) wherein $R^2$ is ($C_1$–$C_4$)alkyl or ($C_3$–$C_7$)cycloalkyl and $R^8$ is benzyl is reacted with hydrogen bromide or hydrogen chloride in a suitable solvent such as acetic acid, propionic acid or the like. The reaction mixture is generally heated at from about 30° C. to about 80° C. with the preferred temperature being about 40° C. to about 50° C. The reaction is generally complete after about two hours, but the reaction time may vary from 15 minutes to 8 hours. When the reaction is complete the product mono ester of formula (I) is isolated according to ordinary procedures of organic chemistry.

Alternatively, to prepare the mono ester compounds of formula (I) of this invention wherein $R^2$ is ($C_1$–$C_4$)alkyl, ($C_3$–$C_7$)cycloalkyl or benzyl and $R^8$ is hydrogen, a compound of formula (IV)

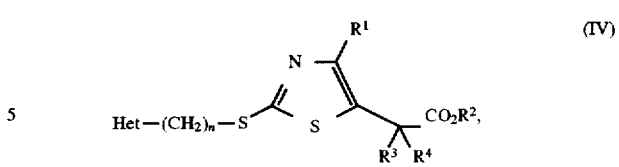

wherein $R^1$, $R^2$, $R^3$, $R^4$, n and Het are defined as in formula (I) hereinabove and $R^8$ is a silyl protecting group or a silylethyl protecting group is reacted under the standard desilylation conditions of organic chemistry. Silyl protecting groups which are useful for protecting esters include triisopropylsilyl, triphenylsilyl, dimethylphenylsilyl, t-butyldimethylsilyl, t-butyldiphenylsilyl, trimethylsilylethyl, triethylsilylethyl, t-butyldimethylsilylethyl, t-butyldiphenylsilylethyl, dimethylphenylsilylethyl, diethylphenylsilylethyl and the like. Thus, a compound of formula (IV) as defined above is reacted with a fluoride source in a reaction inert solvent under a reaction inert atmosphere at 0° C. to about 70° C. Generally good sources of fluoride ion for this reaction include cesium fluoride and tetrasubstituted ammonium fluorides. A particularly preferred fluoride source for its availability and ease of handling is tetra-n-butylammonium fluoride. Reaction inert solvents which are useful for this reaction include chlorinated solvents such as methylene chloride and chloroform; ether solvents such as diethyl ether, tetrahydrofuran and dioxane; N,N-dimethylformamide, dimethylsulfoxide, acetonitrile and the like. A preferred solvent is tetrahydrofuran. Generally the reaction is carried out at room temperature under a nitrogen atmosphere. The reaction times may vary depending upon the reactivity of the substrate and the fluoride source, but generally the reaction is complete within 15 minutes to one hour. Occasionally the reaction will require as much as 24 hours to be complete. The mono ester carboxylic acids generated by this reaction are isolated utilizing the standard techniques of organic chemistry.

Alternatively, the esters and diesters of formula (I) of this invention may be hydrolyzed by reacting a compound of formula (I) wherein $R^2$ and $R^8$ are each independently ($C_1$–$C_4$)alkyl, ($C_3$–$C_7$)cycloalkyl or benzyl and p is 0 under basic conditions in a reaction inert solvent or solvents. Typically the diester compound of formula (I) is dissolved in a reaction inert solvent or combination of solvents and water is added. Suitable reaction inert solvents for this reaction include ethers such as diethyl ether, dioxane, tetrahydrofuran and the like, alcohols such as methanol, ethanol, 1-propanol, 2-propanol and the like. The solution is treated slowly with one equivalent of a suitable base such as potassium carbonate, sodium carbonate, NaOH, KOH and the like. Where the base exists in granular form it is usually useful to pulverize the base by grinding into a powder. Generally the reaction mixture is stirred at room temperature for 4–24 hours however occasionally it will be necessary to heat the reaction mixture to about 50° C. The mono ester compound of formula (I) wherein $R^2$ is H and $R^8$ is ($C_1$–$C_4$) alkyl or ($C_3$–$C_7$)cylcoalkyl is then isolated according to standard practice.

The ester and diester compounds of formula (I) of this invention are readily prepared using standard thio-alkylation and arylation chemistry. Typically, a heterocyclic compound of the formula Het-$(CH_2)_n$—X, wherein Het and n are as defined above; X is halo selected from chloro, bromo or iodo; and $R^8$, if $R^5$ is $CO_2R^8$, is ($C_1$–$C_4$)alkyl or ($C_3$–$C_7$) cycloalkyl; is reacted with a thiazole derivative of formula (V)

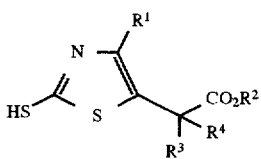

(V)

wherein $R^1$, $R^3$ and $R^4$ are as defined above and $R^2$ is ($C_1$–$C_4$)alkyl or ($C_3$–$C_7$)cycloalkyl and a suitable base in a reaction inert solvent for 8–24 hours at a temperature of about 40° C. to the reflux temperature of the solvent being used. Suitable bases for this reaction include potassium carbonate, sodium carbonate, and sodium hydroxide. Preferred is potassium carbonate. Suitable reaction inert solvents for this reaction include acetone, THF, CHCl$_3$, DMF, CH$_2$Cl$_2$, DMSO, dioxane. The preferred solvent is acetone. The ester and diester compounds of formula (I) are isolated by methods well known to one skilled in the art of organic chemistry.

Alternatively, the compounds of formula (I) of this invention wherein $R^2$ and $R^8$ are each independently ($C_1$–$C_4$)alkyl or ($C_3$–$C_7$)cycloalkyl and the compounds of formula (I) wherein $R^2$ is ($C_1$–$C_4$)alkyl or ($C_3$–$C_7$)cycloalkyl and $R^5$ is not (CH$_2$)$_p$CO$_2$R$^8$ are prepared by reducing the N-oxide compounds of formula (III). To prepare the N-oxide compounds of formula (III), substantially the same procedure as that disclosed in the foregoing paragraph is utilized. Thus, the N-oxide of the compound of formula Het-(CH$_2$)$_n$—X, wherein n and X are as defined above and Het is pyridyl, pyrimidinyl, pyrazinyl, pyridazinyl, quinolinyl, isoquinolinyl, cinnolinyl, thiazolyl, benzothiazolyl, quinoxalinyl or quinazolinyl and Het is substituted as described hereinabove by $R^5$, $R^6$ and $R^7$, is reacted with a thiazole derivative of the formula (V), defined hereinabove, and a suitable base in a reaction inert solvent for 8–24 hours at a temperature of about 40° C. to about the reflux temperature of the solvent being used. Suitable bases for this reaction include potassium carbonate, sodium carbonate, and sodium hydroxide. The preferred base is potassium carbonate. Suitable reaction inert solvents for this reaction include acetone, THF, CHCl$_3$, DMF, DMSO, CH$_2$Cl$_2$, and dioxane. The preferred solvent is acetone. The N-oxide coupled product of the reaction is isolated according to the standard procedures or organic chemistry.

The N-oxide compounds of formula (III) of this invention are reduced, as disclosed hereinabove, conveniently to afford the diester and monoester compounds of formula (I) of this invention. Thus, the N-oxide compounds of formula (III) of this invention are dissolved in a suitable reaction inert solvent and cooled to –20° C. to 5° C. The preferred temperature for this reaction is 0° C. A suitable reducing agent such as phosphorous trichloride or triphenylphosphine is dissolved in a suitable reaction inert solvent and is added to the solution containing the N-oxide derivative. The addition generally must be carried out carefully, keeping the temperature of the reaction mixture below about 5° C. The reaction mixture is stirred for 10 minutes to 2 hours at 0° C. and for about 16 hours at room temperature. The diester and monoester compounds of formula (I) are isolated according to the standard methods of organic chemistry.

The thiazole derivative of the formula (V), defined hereinabove, is prepared by methods well known to those skilled in the art or by the method described in Fleischmann et al., Arzneim-Forsch./Drug. Res. 1989, 39(II), 743.

The N-oxide of the compound of formula Het-(CH$_2$)$_n$—X, wherein n and X are as defined above, Het is a heterocyclic group containing a nitrogen atom selected from pyridyl, pyrimidinyl, pyrazinyl, pyridazinyl, quinolinyl, isoquinolinyl, cinnolinyl, thiazolyl, benzothiazolyl, quinoxalinyl, or quinazolinyl, and Het is substituted by $R^5$, $R^6$ and $R^7$ and described hereinabove is readily prepared by oxidation of the corresponding heterocyclic derivative. Thus a heterocyclic compound of the formula Het-(CH$_2$)$_n$—X, as defined hereinabove, containing a free nitrogen atom, is dissolved in a suitable reaction inert solvent and is treated with an oxidizing agent such as meta-chloroperbenzoic acid or hydrogen peroxide. The reaction is generally carried out at room temperature but occasionally it will be necessary to maintain the temperature of the reaction mixture below room temperature, such as at 0° C. The oxidizing agent is added to the reaction mixture as a solid or a liquid or, alternatively, the oxidizing agent is added as a solution in a reaction inert solvent. Suitable reaction inert solvents for this reaction include solvents such as dichloromethane, chloroform, carbon tetrachloride, or trifluoroacetic acid.

To prepare the compounds of formula (IV) wherein $R^1$, $R^2$, $R^3$, $R^4$, n and Het are as defined hereinabove for formula (IV), a compound of the formula Het-(CH$_2$)$_n$—X, wherein X, n and Het are as defined hereinabove and $R^8$ is H, is reacted with a silyl compound containing one leaving group or with a silylethanol derivative. The reaction is carried out in a reaction inert solvent or solvent system in the presence of an organic base at 0° C. to about 80° C. Suitable silyl compounds containing one good leaving group include, but are not limited to, dimethylphenylsilylchloride, t-butyldimethylsilylchloride, t-butyldiphenylsilylchloride, and the like. Suitable silylethanol derivatives include trimethylsilylethanol, triethylsilylethanol, t-butyldimethylsilylethanol and the like. Reaction inert solvents for this reaction include acetonitrile, N,N-dimethylformamide, dimethylsulfoxide, ether solvents such as diethyl ether, tetrahydrofuran, dioxane and the like. A particularly preferred solvent system for this reaction is acetonitrile and N,N-dimethylformamide. Organic bases include but are not limited to such bases as pyridine, trimethylamine, triisopropylamine, piperidine and the like. Pyridine is preferred. When the reaction utilizes a silylethanol derivative, it is sometimes necessary to use an activating group such as 1,3-dicyclohexylcarbodiimide to activate the carboxylic acid. The reagents are generally mixed at 0° C. and the reaction mixture is warmed slowly to room temperature. The reaction may be stirred at room temperature for up to 24 hours but is generally complete after stirring for one to sixteen hours. The compound of the formula Het-(CH$_2$)$_n$—X wherein $R^8$ is protected is isolated according to standard techniques of organic chemistry. The compound of the formula Het-(CH$_2$)$_n$—X is then coupled as described hereinabove to afford a compound of formula (IV) wherein $R^8$ is a silyl protecting group or a silylethyl protecting group.

The compounds of the formula Het-(CH$_2$)$_n$—X, wherein Het and n are as defined above and X is fluoro, chloro or bromo, are prepared according to standard methods of organic chemistry or are readily available from well-known suppliers such as Aldrich, Sigma, Lancaster and the like.

Where the compounds of formula (I) of this invention contain free carboxylic acids, such as when $R^2$ is H or when $R^2$ and $R^8$ are each H, pharmaceutically acceptable cationic salts of the compounds can be prepared.

The expression "pharmaceutically-acceptable cationic salts" is intended to define but is not limited to such salts as the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine) diethylamine, piperazine, tromethamine (2-amino-2-hydroxymethyl-1,3-propanediol) and procaine.

Where the compounds of formula (I) of this invention contain basic nitrogen atoms, such as nitrogen-containing heterocyclic atoms, pharmaceutically acceptable acid addition salts of the compounds can be prepared.

The expression "pharmaceutically-acceptable acid addition salts" is intended to define but is not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

The pharmaceutically-acceptable cationic salts of the compounds of the present invention are readily prepared by reacting the acid forms with an appropriate base, usually one equivalent (also can be 2 quivalents for diacids), in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The present compounds of formula (I) of this invention are readily adapted to clinical use as antiviral agents. Said antiviral utility is demonstrated by activity in the following in vivo screen.

Female C57/B6 mice are infected with a sublethal dose of influenza A intranasally using metaphane as the anesthetic. The compounds to be tested are administered daily orally (PO) or intraperitoneally (IP) beginning either immediately after infection or three days later. Lung viral titers are determined four to six days after infection by assessing hemagluttinin activity in supernatants of serially diluted and infected MDCK cells. A t test for significance (p<0.05) is used to determine the activity of compound treated animals versus their respective placebo tested controls. A total of 10 animals are used for each test group. In addition, some compounds are evaluated against a lethal rather than sublethal inoculum of virus using survival as the endpoint. Further the viral challenge can be administered via aerosol rather than intranasally. When lethal doses of viral inoculum are administered, the significance is assessed using the Fishers Exact Test and the compound is administered one day prior to and on the day of infection.

The present compounds of formula (I) of this invention are clinically administered to mammals, including man, via either the oral or parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is desirable that the drug be administered parenterally. By either route, the dosages are in the range of about 0.01 to about 50 mg/kg body weight of the subject per day, and preferably about 0.1 to about 5 mg/kg body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

The compounds can be used in pharmaceutical preparations containing the compound, or pharmaceutically acceptable acid salts thereof, in combination with a pharmaceutically acceptable carrier or diluent. Suitable pharmaceutically acceptable carriers include inert solid fillers or diluents and sterile aqueous or organic solutions. The active compound will be present in such pharmaceutical compositions in amounts in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions of suspensions. For example, suspensions or solutions in sesame or peanut oil, aqueous propylene glycol and the like can be used, as well as aqueous solutions of water-soluble pharmaceutically acceptable salts of the compounds. The solutions prepared in this manner can then be administrated intravenously, intraperitoneally, subcutaneously, or intramuscularly, with intramuscular administration being the preferred parenteral route in man.

The following terms and phrases, when used herein and in the appendant claims, are defined as follows:

1. "Alkyl" means a branched or unbranched saturated hydrocarbon group containing the specified number of carbon atoms, e.g., $C_1-C_8$. Examples include, but are not limited to methyl, ethyl, isopropyl, n-butyl, t-butyl and the like.

2. "Alkoxy" means a branched or unbranched saturated hydrocarbon containing the specified number of carbon atoms and a single oxygen atom by which said hydrocarbon is attached to a central backbone. Examples include, but are not limited to methoxy, ethoxy and the like.

3. Reaction inert solvent means a solvent which does not interact with the reactants, intermediates or products in such a way that adversely affects the yield of the desired products.

4. "Parenteral" means a mode of administration other than through the gastrointestinal tract. Parenteral modes of administration thus include but are not limited to intravenous, subcutaneous, intramuscular, intramedullary, transdermal and iontophoretic.

The present invention is illustrated by the following examples. However, it should be understood that the invention is not limited to the specific details of these examples. All reactions are conducted under an inert atmosphere, such as nitrogen or argon, unless otherwise specified. All solvents are anhydrous, i.e., contain such a small amount of water that said water does not interact with the reagents, intermediates or products in such a way that adversely affects the yield of the desired products. Where used herein, "THF" means tetrahydrofuran. "DMF" means N,N-dimethylformamide. "DMSO" means dimethyl sulfoxide and "mCPBA" means meta-chloroperbenzoic acid.

EXAMPLE 1

2-((5-(2-Ethoxy-2-oxoethyl)-4-methyl-2-thiazolyl) thio)-3-pyridinecarboxylic Acid Ethyl Ester A solution of 12.3 g (0.032 mol) of the compound of Preparation 23 in 200 ml of dichloromethane was cooled to 0° C. and treated dropwise with 15.5 ml (0.031 mol) of a 2M dichloromethane solution of phosphorous trichloride while maintaining an internal temperature below 5° C. The mixture was stirred at 0° C. for 10 min and then at room temperature for 16 hours. The mixture was evaporated and the residue was partitioned between ethyl acetate and saturated aqueous sodium bicarbonate solution. Drying ($Na_2SO_4$) of the organic layer, evaporation, and purification of the residue by flash chromatography with an ethyl acetate-hexane (1:1) eluant afforded 8.4 g (71%) of the title compound of this Example. mp 181°–183° C. $^1$H NMR ($CDCl_3$): δ 1.26 (3H, t, J=7), 1.41 (3H, t, J=7), 2.40 (3H, s), 3.77 (2H, s), 4.18 (2H, q, J=7), 4.42 (2H, q, J=7), 7.13 (1H, dd, J=8, 5), 8.26 (1H, dd, J=8, 2), 8.51 (1H, dd, J=5, 2).

EXAMPLES 2-10

Utilizing substantially the same procedure as recited in Example 1, but substituting the appropriate starting material for the compound of Preparation 23, the following compounds were prepared.

2. 2-((5-(2-Ethoxy-2-oxoethyl)-4-methyl-2-thiazolyl)thio)-4-methyl-3-pyridinecarboxylic Acid Ethyl Ester Prepared from the title compound of Preparation 26. mp 85°–87° C. $^1$H NMR ($CDCl_3$): δ 1.23 (3H, t, J=7), 1.40 (3H, t, J=7), 2.34 (3H, s), 2.38 (3H, s), 3.70 (2H, s), 4.14 (2H, q, J=7), 4.41 (2H, q, J=7), 6.96 (1H, d, J=5), 8.32 (1H, d, J=5).

3. 2-((5-(2-Ethoxy-2-oxoethyl)-4-methyl-2-thiazolyl)thio)-6-methyl-3-pyridinecarboxylic Acid Ethyl Ester Prepared from the title compound of Preparation 27. mp 95°–97° C. $^1$H NMR ($CDCl_3$): δ 1.25 (3H, t, J=7), 1.40 (3H, t, J=7), 2.38 (3H, s), 2.54 (3H, s), 3.75 (2H, s), 4.17 (2H, q, J=7), 4.39 (2H, q, J=7), 6.98 (1H, d, J=8), 8.15 (1H, d, J=8).

4. 2-((5-(2-Ethoxy-2-oxoethyl)-4-methyl-2-thiazolyl)thio)-3-pyridineacetic Acid Ethyl Ester Prepared from the title compound of Preparation 29. $^1$H NMR ($CDCl_3$): δ 1.24 (6H, t, J=7), 2.35 (3H, s), 3.70 (2H, s), 3.77 (2H, s), 4.15 (2H, q, J=7), 4.16 (2H, q, J=7), 7.15 (1H, dd, J=8, 5), 7.55 (1H, d, J=8), 8.44 (1H, d, J=5).

5. 2-((5-(2-Ethoxy-2-oxoethyl)-4-methyl-2-thiazolyl)thio)-4-pyridinecarboxylic Acid Methyl Ester Prepared from the title compound of Preparation 24. mp 52°–54° C. $^1$H NMR ($CDCl_3$): δ 1.25 (3H, t, J=7), 2.39 (3H, s), 3.75 (2H, s), 3.90 (3H, s), 4.17 (2H, q, J=7), 7.60 (1H, dd, J=5, 1), 7.78 (1H, s), 8.58 (1H, dd, J=5, 2).

6. 6-((5-(2-Ethoxy-2-oxoethyl)-4-methyl-2-thiazolyl)thio)-2-pyridinecarboxylic Acid Ethyl Ester Prepared from the title compound of Preparation 33. mp 73°–75° C. $^1$H NMR ($CDCl_3$): δ 1.26 (3H, t, J=7), 1.43 (3H, t, J=7), 2.41 (3H, s), 3.76 (2H, s), 4.16 (2H, q, J=7), 4.45 (2H, q, J=7), 7.38 (1H, d, J=7), 7.69 (1H, t, J=8), 7.90 (1H, d, J=8). Analysis calculated for $C_{16}H_{18}N_2O_4S$: C 52.44; H 4.95; N 7.64. Found: C 52.52; H 4.91; N 7.50.

7. 4-Methyl-2-(2-pyridinylthio)-5-thiazoleacetic Acid Ethyl Ester

Prepared from the title compound of Preparation 28. $^1$H NMR ($CDCl_3$): δ 1.22 (3H, t, J=7), 2.35 (3H, s), 3.71 (2H, s), 4.14 (2H, q, J=7), 7.03–7.09 (1H, m), 7.20 (1H, d, J=8), 7.52 (1H, dt, J=8, 2), 8.41–8.43 (1H, m).

8. 2-((5-(2-Ethoxy-2-oxoethyl)-4-methyl-2-thiazolyl)thio)-5-methyl-3-pyridinecarboxylic Acid Ethyl Ester Prepared from the title compound of Preparation 25. $^1$H NMR ($CDCl_3$): δ 1.24 (3H, t, J=7), 1.43 (3H, t, J=7), 2.33 (3H, s), 2.41 (3H, s), 3.78 (2H, s), 4.19 (2H, q, J=7), 4.43 (2H, q, J=7), 8.07 (1H, s), 8.36 (1H, s).

9. 2-((5-(2-Ethoxy-2-oxoethyl)-4-methyl-2-thiazolyl)thio)-3-trifluoromethylpyridine Prepared from the title compound of Preparation 30. Anal calcd. for $C_{14}H_{13}F_3N_2O_2S_2$: C 46.40; H 3.62; N 7.73. Found: C 46.20; H 3.33; N 7.68. m/e calcd for $C_{14}H_{13}F_3N_2O_2S_2$: 362.3951. Found: 362.03441.

10. 2-((5-(2-Ethoxy-2-oxoethyl)-4-methyl-2-thiazolyl)thio)-4-trifluoromethylpyridine Prepared from the title compound of Preparation 31. mp 57°–59° C. Analysis calcd for $C_{14}H_{13}F_3N_2O_2S_2$: C 46.40; H 3.62; N 7.73. Found: C 46.29; H 3.43; N 7.52. m/e calcd for $C_{14}H_{13}F_3N_2O_2S_2$: 362.3951. Found: 362.03150.

EXAMPLE 11

2-((5-(2-Ethoxy-2-oxoethyl)-4-methyl-2-thiazolyl) thio)-5-trifluoromethylpyridine 2-Chloro-5-trifluoromethylpyridine (Ishihara Corporation, 600 Montgomery St., San Francisco, Calif. 94111) (0.5 g, 2.8 mmol) and 5-(2-ethoxy-2-oxoethyl)-2-mercapto-4-methyl-1,3-thiazole (K. Fleishmann, K. H. Scheunemann, H. U. Schortemmer, G. Dickneite, J. Blumbad, G. F. Fischer, W. Durckheimer, and H. H. Sedlacek, Arzneim-Forsch./Drug Res., 1989, 39(II), 743) (0.6 g, 2.8 mmol) were dissolved in acetone (15 ml) under a reaction inert atmosphere. Freshly ground $K_2CO_3$ (0.42 g, 3.0 mmol) was added to this solution and the reaction was heated to 65° C. for 16 hours. The $K_2CO_3$ was filtered off and the acetone was removed via rotary evaporation. The remaining slurry was diluted with a saturated aqueous solution of sodium bicarbonate, extracted three times (200 ml) with methylene chloride, dried over $MgSO_4$ and filtered. The solvent was then stripped off and the resulting solid was purified via flash chromatography (50% ether in hexane) to afford the title compound of this Example (0.57 g, 57% yield). $^1$H NMR ($CDCl_3$): δ 8.69 (1H, d, J=2), 7.75 (1H, dd, J=8,2), 7.29 (1H, d, J=8), 4.20 (2H, q, J=7), 3.79 (2H, s), 2.43 (3H, s), 1.28 (3H, t, J=7).

EXAMPLES 12–28

Utilizing substantially the same procedure as recited in Example 11, but substituting the appropriate starting material in place of 2-chloro-5-trifluoromethyl pyridine, the following compounds were prepared.

12. 2-((5-(2-Ethoxy-2-oxoethyl)-4-methyl-2-thiazolyl)thio)-3-pyridinecarboxylic Acid Methyl Ester Prepared from 2-chloronicotinic acid methyl ester (Sugasawa, et al. J. Pharm. Soc. Jpn. 1952, 72, 1336) mp 79°–80° C. $^1$H NMR (CDCl$_3$): δ 1.24 (3H, t, J=7), 2.43 (3H, s), 3.76 (s, 2H), 3.93 (3H, s), 4.16 (2H, q, J=7), 7.12–7.23 (1H, m), 8.26 (1H, d, J=7), 8.48–8.56 (1H, m).

13. 2-((5-(2-Ethoxy-2-oxoethyl)-4-methyl-2-thiazolyl)thiomethyl)-3-pyridinecarboxylic Acid Ethyl Ester Prepared from 2-bromomethyl-3-pyridinecarboxylic acid ethyl ester hydrochloride (prepared according to the method of Clarke, et al., J. Chem. Soc., Perkin Trans. I, 1984, 1501). The reaction was carried out at room temperature. $^1$H NMR (CDCl$_3$): δ 1.21 (3H, t, J=7), 1.36 (3H, t, J=7), 2.26 (3H, s), 3.61 (2H, s), 4.11 (2H, q, J=7), 4.35 (2H, q, J=7), 4.89 (2H, s), 7.25 (1H, dd, J=7, 5), 8.21 (1H, dd, J=8, 2), 8.59 (1H, dd, J=5, 2).

14. 3-((5-(2-Ethoxy-2-oxoethyl)-4-methyl-2-thiazolyl)thiomethyl)-4-pyridinecarboxylic Acid Ethyl Ester Prepared from 3-chloromethyl-4-pyridine carboxylic acid ethyl ester (prepared by the method of Clarke, supra). The reaction was carried out at room temperature. $^1$H NMR (CDCl$_3$): δ 1.22 (3H, t, J=7),1.41 (3H, t, J=7), 2.30 (3H, s), 3.62 (2H, s), 4.13 (2H, q, J=7), 4.39 (2H, q, J=7), 4.70 (2H, s), 7.73 (1H, d, J=5), 8.60 (1H, d, J=5), 8.69 (1H, s).

15. 4-((5-(2-Ethoxy-2-oxoethyl)-4-methyl-2-thiazolyl)thiomethyl)-3-pyridinecarboxylic Acid Ethyl Ester Prepared from 4-chloromethyl-3-pyridine carboxylic acid ethyl ester (prepared by the method of Clarke, supra). The reaction was carried out at room temperature. $^1$H NMR (CDCl$_3$): δ 1.23 (3H, t, J=7), 1.40 (3H, t, J=7), 2.29 (3H, s), 3.63 (2H, s), 4.13 (2H, q, J=7), 4.40 (2H, q, J=7), 4.71 (2H, s), 7.36 (1H, d, J=7), 8.54 (1H, d, J=7), 9.08 (1H, s).

16. 2-((5-(2-Methoxy-2-oxoethyl)-4-methyl-2-thiazolyl)thiol-5-pyridinecarboxylic Acid Methyl Ester Prepared from the title compound of Preparation 38. Transesterification occurred due to the presence of methanol stabilizer in the batch of acetone which was used. mp 132° C.–134° C. $^1$H NMR (CDCl$_3$): δ 2.50 (3H, s), 3.75 (3H, s), 3.85 (2H, s), 3.92 (3H, s), 7.42 (1H, d, J=7), 8.22 (1H, d, J=7), 9.11 (1H, s).

17. 4-((5-(2-Ethoxy-2-oxoethyl)-4-methyl-2-thiazolyl)thio)-2-methylmercaptopyrimidine Prepared from 4-chloro-2-methylmercaptopyrimidine (Aldrich, 1001 West Saint Paul Avenue, Milwaukee, Wis., 53233 USA). mp 68°–72° C. Analysis calculated for C$_{13}$H$_{15}$N$_3$O$_2$S$_3$: C 45.73; H 4.43; N 12.31. Found: C 45.76; H 4.35; N 12.18. m/e calculated for C$_{13}$H$_{15}$N$_3$O$_2$S$_3$: 341.4754. Found: 341.03424.

18. 6-((5-(2-Ethoxy-2-oxoethyl)-4-methyl-2-thiazolyl)thio)-2-methylmercaptopyrimidine-4-carboxylic Acid Ethyl Ester Prepared from 4-chloro-2-methylmercaptopyrimidine-6-carboxylic acid ethyl ester (Sigma Chemical Company, P.O. Box 14508, St. Louis, Mo. 63178 USA). mp 69°–71° C. Analysis calculated for C$_{16}$H$_{19}$N$_3$O$_4$S$_3$: C 46.47; H 4.63; N 10.16. Found: C 46.43; H 4.50; N 10.01. m/e calculated for C$_{16}$H$_{19}$N$_3$O$_4$S$_3$: 413.5395. Found: 413.05030.

19. 4-((5-(2-Ethoxy-2-oxoethyl)-4-methyl-2-thiazolyl)thio)-2,6-dimethoxypyrimidine Prepared from 4-chloro-2,6-dimethoxypyrimidine (Aldrich, 1001 West Saint Paul Avenue, Milwaukee, Wis., 53233 USA). $^1$H NMR (DMSO-d$_6$): 66.32 (1H, s), 4.15 (2H, q, J=7), 4.00 (2H, s), 3.88 (6H, s), 2.35 (3H, s), 1.21 (3H, t, J=7).

20. 3-((5-(2-Ethoxy-2-oxoethyl)-4-methyl-2-thiazolyl)thio)-6-methoxypyridazine Prepared from 3-chloro-6-methoxypyridazine (Aldrich, 1001 West Saint Paul Avenue, Milwaukee, Wis., 53233 USA). mp 47°–49° C. Analysis calculated for C$_{13}$H$_{15}$N$_3$O$_3$S$_2$: C 47.98; H 4.65; N 12.91. Found: C 48.06; H 4.63; N 12.64. m/e calculated for C$_{13}$H$_{15}$N$_3$O$_3$S$_2$: 325.4108. Found: 325.05640.

21. 4-((5-(2-Ethoxy-2-oxoethyl)-4-methyl-2-thiazolyl)thio)quinoline-2-carboxylic Acid Methyl Ester Prepared from the title compound of Preparation 16. mp 94°–95° C. Analysis calculated for C$_{19}$H$_{18}$N$_2$O$_4$S$_2$: C 56.70; H 4.51; N 6.96. Found: C 56.55; H 4.31; N 6.89. m/e calculated for C$_{19}$H$_{18}$N$_2$O$_4$S$_2$: 402.4943. Found: 402.06730.

22. 4-((5-(2-Ethoxy-2-oxoethyl)-4-methyl-2-thiazolyl)thio)-8-methoxyquinoline-2-carboxylic Acid Ethyl Ester Prepared from the title compound of Preparation 14. mp 120°–121° C. Analysis calculated for C$_{21}$H$_{22}$N$_2$O$_5$S$_2$: C 56.49; H 4.97; N 6.27. Found: C 56.48; H 4.94; N 6.26. m/e calculated for C$_{21}$H$_{22}$N$_2$O$_5$S$_2$: 446.5479. Found: 446.09510.

23. 1-Chloro-3-((5-(2-ethoxy-2-oxoethyl)-4-methyl-2-thiazolyl)thio)isoquinoline Prepared from 1,3-dichloroisoquinoline (Bader, 1001 West Saint Paul Avenue, Milwaukee, Wis., 53233 USA). mp 115°–117° C. Analysis calculated for C$_{17}$H$_{15}$ClN$_2$O$_2$S$_2$: C 53.89; H 3.99; N 7.39. Found: C 53.84; H 3.79; N 7.33. m/e calculated for C$_{17}$H$_{15}$ClN$_2$O$_2$S$_2$: 378.9023. Found: 378.02746.

24. 3-(2-Ethoxy-2-oxoethyl)-2-((5-(2-ethoxy-2-oxoethyl)-4-methyl-2-thiazolyl)thio)-1,4-quinoxaline Prepared from the title compound of Preparation 18. mp 75°–77° C. Analysis calculated for C$_{20}$H$_{21}$N$_3$O$_4$S$_2$: C 55.67; H 4.91; N 9.74. Found: C 55.46; H 5.07; N 9.64. m/e calculated for C$_{20}$H$_{21}$N$_3$O$_4$S$_2$: 431.5361. Found: 431.09842.

25. 6-((5-(2-Ethoxy-2-oxoethyl)-4-methyl-2-thiazolyl)thiomethyl)-4-hydroxy-2-methylpyrimidine Prepared from 6-chloromethyl-4-hydroxy-2-methylpyrimidine (Bader, 1001 West Saint Paul Avenue, Milwaukee, Wis., 53233 USA). mp 131°–132° C. Analysis calculated for $C_{14}H_{17}N_3O_3S_2$: C 49.54; H 5.05; N 12.38. Found: C 49.55; H 4.76; N 12.10. m/e calculated for $C_{14}H_{17}N_3O_3S_2$: 339.4379. Found: 339.07843.

26. 6-((5-(2-Ethoxy-2-oxoethyl)-4-methyl-2-thiazolyl)thiomethyl)-2,4-dihydroxypyrimidine Prepared from 6-chloromethyl-2,4-dihydroxypyrimidine (Aldrich, 1001 West Saint Paul Avenue, Milwaukee, Wis., 53233 USA). mp 203°–204° C. Analysis calculated for $C_{13}H_{15}N_3O_4S_2$: C 45.74; H 4.43; N 12.31. Found: C 45.59; H 4.28; N 12.14. m/e calculated for $C_{13}H_{15}N_3O_4S_2$: 341.4102. Found: 341.04547.

27. 5-((5-(2-Ethoxy-2-oxoethyl)-4-methyl-2-thiazolyl)thiomethyl)thiophene-2-carboxylic Acid Methyl Ester Prepared from the title compound of Preparation 20. mp 49°–51° C. Analysis calculated for $C_{15}H_{17}NO_4S_3$: C 48.50; H 4.61; N 3.77. Found: C 48.49; H 4.69; N 3.56. m/e calculated for $C_{15}H_{17}NO_4S_3$: 371.4990. Found: 371.03379.

28. 2-((5-(2-Ethoxy-2-oxoethyl)-4-methyl-2-thiazolyl)thio)quinoline-4-carboxylic Acid Methyl Ester Prepared from the title compound of Preparation 17. mp 128°–131° C. Analysis calculated for $C_{19}H_{18}N_2O_4S_2$: C 56.70; H 4.51; N 6.96. Found: C 56.32; H 4.21; N 6.81. m/e calculated for $C_{19}H_{18}N_2O_4S_2$: 402.4943. Found: 402.07288.

EXAMPLE 29

2-((5-Carboxymethyl-4-methyl-2-thiazolyl)thio)-3-pyridinecarboxylic Acid

To a mixture of 737 mg (2.09 mmol) of the title compound of Example 1, 70 ml of methanol, and 30 ml of water chilled to 0° C. in an ice bath was added 210 mg (5.22 mmol, 2.5 equivalents) of sodium hydroxide. After the sodium hydroxide had dissolved, the ice bath was removed and the mixture was allowed to stir at room temperature for 3 hours. The solvent was removed by rotary evaporation and the residue was diluted with water, chilled to 0° C. in an ice bath, and acidified with aqueous 6N HCl solution until precipitation had ceased. The precipitate was collected by filtration (washed with cold water) and was dried under vacuum to yield 554 mg (85%) of the title compound, mp 233°–235° C. $^1$H NMR (DMSO-d$_6$): δ 2.29 (3H, s), 3.85 (2H, s), 7.38 (1H, dd, J=8, 5), 8.33 (1H, d, J=8), 8.63 (1H, d, J=5). FAB MS (m/e): 311 (M$^+$+1), 265, 233, 119 (base).

EXAMPLES 30–51

Utilizing substantially the same procedure as recited in Example 29, but substituting the appropriate starting material for the title compound of Example 1, the following compounds were prepared.

30. 2-((5-Carboxymethyl-4-methyl-2-thiazolyl)thio)-4-methyl-3-pyridinecarboxylic Acid Prepared from the title compound of Example 2. The reaction was additionally altered from the procedure of Example 29 by stirring the reaction mixture for 17 hours and the addition of an extra 4 eq. of sodium hydroxide 1 hour prior to workup. mp 208°–210° C. $^1$H NMR (DMSO-d$_6$): δ 2.27 (3H, s), 2.40 (3H, s), 3.83 (2H, s), 7.26 (1H, d, J=5), 8.42 (1H, d, J=5). MS (m/e): 324 (M$^+$), 169 (base), 151, 122, 105.

31. 2-((5-Carboxymethyl-4-methyl-2-thiazolyl)thio)-6-methyl-3-pyridinecarboxylic Acid Prepared from the title compound of Example 3. mp 223°–225° C. $^1$H NMR (DMSO-d$_6$): δ 2.28 (3H, s), 2.58 (3H, s), 3.82 (2H, s), 7.27 (1H, d, J=8), 8.24 (1H, d, J=8). MS (m/e): 324 (M$^+$), 316, 279.

32. 2-((5-Carboxymethyl-4-methyl-2-thiazolyl)thio)-3-pyridineacetic Acid

Prepared from the title compound of Example 4. mp 172°–174° C. $^1$H NMR (DMSO-d$_6$): δ 2.25 (3H, s), 3.78 (2H, s), 3.81 (2H, s), 7.34 (1H, dd, J=8, 5), 7.77 (1H, dd, J=8, 2), 8.46 (1H, dd, J=6, 2). MS (m/e): 324 (M$^+$), 291, 280, 261, 247, 189, 144, 135 (base).

33. 2-((5-Carboxymethyl-4-methyl-2-thiazolyl)thio)-4-pyridinecarboxylic Acid Prepared from the title compound of Example 5. mp 212°–214° C. $^1$H NMR (DMSO-d$_6$): δ 2.32 (3H, s), 3.89 (2H, s), 7.67 (1H, dd, J=5, 1), 7.71 (1H, s), 8.67 (1H, d, J=5, 1). MS (m/e): 311 (M$^+$+1), 155, 135, 119 (base).

34. 2-((5-Carboxymethyl-4-methyl-2-thiazolyl)thio)-5-pyridinecarboxylic Acid Prepared from the title compound of Example 16. mp 226°–228° C. $^1$H NMR (DMSO-d$_6$): δ 2.34 (3H, s), 3.91 (2H, s), 7.37 (1H, dd, J=8, 1), 8.19 (1H, dd, J=8, 1), 8.93 (1H, dd, J=2, 1). MS (m/e): 310 (M$^+$), 260 (base), 151.

35. 2-((5-Carboxymethyl-4-methyl-2-thiazolyl)thio)-6-pyridinecarboxylic Acid Prepared from the title compound of Example 6. mp 211°–213° C. $^1$H NMR (DMSO-d$_6$): δ 2.31 (3H, s), 3.88 (2H, s), 7.46 (1H, dd, J=8, 1), 7.89–7.98 (2H, m). MS (m/e): 310 (M$^+$), 265 (base), 219, 112.

36. 4-Methyl-2-(2-pyridinylthio)-5-thiazoleacetic Acid

Prepared from the title compound of Example 7. mp 140°–142° C. $^1$H NMR (DMSO-d$_6$): δ 2.31 (3H, s), 3.87 (2H, s), 7.28–7.38 (2H, m), 7.76–7.82 (1H, m), 8.51–8.53 (1H, m). MS (m/e): 266 (M$^+$), 221, 78.

37. 2-((5-Carboxymethyl-4-methyl-2-thiazolyl)thiomethyl)-3-pyridinecarboxylic Acid Prepared from the title compound of Example 13. mp 225°–227° C. $^1$H NMR (DMSO-d$_6$): δ 2.21 (3H, s), 3.74 (2H, s), 4.91 (2H, s), 7.45 (1H, dd, J=8, 5), 8.25 (1H, dd, J=8, 2), 8.64 (1H, dd, J=8, 2). MS (m/e): 280 (M$^+$—CO2), 189, 135, 106 (base), 78.

38. 3-((5-Carboxymethyl-4-methyl-2-thiazolyl)thiomethyl)-4-pyridinecarboxylic Acid Prepared from the title compound of Example 14. mp 207°–211° C. $^1$H NMR (DMSO-d$_6$): δ 2.22 (3H, s), 3.73 (2H, s), 4.74 (2H, s), 7.91 (1H, d, J=5), 8.73 (1H, d, J=5), 8.84 (1H, s). MS (m/e): 324 (M$^+$), 188, 135 (base).

39. 2-((5-Carboxymethyl-4-methyl-2-thiazolyl)thio)-5-methyl-3-pyridinecarboxylic Acid Prepared from the title compound of Example 8. mp 229°–231° C. $^1$H NMR (DMSO-d$_6$): δ 2.27 (3H, s), 2.31 (3H, s), 3.82 (2H, s), 8.15 (1H, s), 8.48 (1H, s). MS (m/e): 324 (M$^+$), 278, 235, 219, 78 (base), 62.

40. 4-((5-Carboxymethyl-4-methyl-2-thiazolyl)thiomethyl)-3-pyridinecarboxylic Acid Prepared from the title compound of Example 15. mp 178°–180° C. $^1$H NMR (DMSO-$d_6$): δ 2.23 (3H, s), 3.74 (3H, s), 4.74 (2H, s), 7.49 (1H, d, J=5), 8.63 (1H, d, J=5), 8.99 (1H, s). MS (m/e): 324 (M$^+$), 306, 189 (base), 144.

41. 2-((5-Carboxymethyl-4-methyl-2-thiazolyl)thio)-4-methyl-3-pyridine carboxylic Acid Methyl Ester Prepared from the title compound of Example 2 along with the formation of the title compound of Example 30. mp 172°–174° C. $^1$H NMR (DMSO-$d_6$) δ 2.27 (3H, s), 2.37 (3H, s), 3.83 (2H, s), 3.94 (3H, s), 7.30 (1H, d, J=5), 8.46 (1H, d, J=5); MS (m/e) 338(M$^+$), 293, 279.

42. 2-((5-Carboxymethyl-4-methyl-2-thiazolyl)thio)-3-trifluoromethylpyridine Prepared from the title compound of Example 9. mp 195°–196° C. Anal. calcd. for $C_{12}H_9F_3N_2O_2S_2$: C 43.11; H 2.71; N 8.38. Found: C 42.99; H 2.51; N 8.44. m/e calcd for $C_{12}H_9F_3N_2O_2S_2$: 334.3409. Found: 334.01382.

43. 2-((5-Carboxymethyl-4-methyl-2-thiazolyl)thio)-4-trifluoromethylpyridine Prepared from the title compound of Example 10. mp 122°–123° C. Analysis calculated for $C_{12}H_9F_3N_2O_2S_2$: C 43.11; H 2.71; N 8.38. Found: C 42.99; H 2.65; N 8.03. m/e calculated for $C_{12}H_9F_3N_2O_2S_2$: 334.3409. Found: 334.00623.

44. 2-((5-Carboxymethyl-4-methyl-2-thiazolyl)thio)-5-trifluoromethylpyridine Prepared from the title compound of Example 11. mp 113°–114° C. Analysis calculated for $C_{12}H_9F_3N_2O_2S_2$: C 43.11; H 2.71; N 8.38. Found: C 42.73; H 2.45; N 8.28.

45. 2-((5-Carboxymethyl-4-methyl-2-thiazolyl)thio)-6-trifluoromethylpyridine Prepared from the title compound of Example 63 hereinbelow. mp 162°–164° C. Analysis calculated for $C_{12}H_9F_3N_2O_2S_2$: C 43.11; H 2.71; N 8.38. Found: C 43.00; H 2.57; N 8.23. m/e calculated for $C_{12}H_9F_3N_2O_2S_2$: 334.3409. Found: 334.00674.

46. 6-((5-(2-Methoxy-2-oxoethyl)-4-methyl-2-thiazolyl)thio)-2-methylmercaptopyrimidine-4-carboxylic Acid Methyl Ester Prepared from the title compound of Example 18. mp 131°–133° C. m/e calculated for $C_{14}H_{15}N_3O_4S_3$: 385.4854. Found: 385.02111.

47. 3-((5-Carboxymethyl-4-methyl-2-thiazolyl)thio)-6-methoxypyridazine

Prepared from the title compound of Example 20. mp 143°–144° C. m/e calculated for $C_{11}H_{11}N_3O_3S_2$: 297.3566. Found: 297.03080.

48. 4-((5-Carboxymethyl-4-methyl-2-thiazolyl)thio)quinoline-2-carboxylic Acid Prepared from the title compound of Example 21. mp 219°–220° C. m/e calculated for $C_{16}H_{12}N_2O_4S_2$: 360.4130. Found: 360.00759.

49. 4-((5-Carboxymethyl-4-methyl-2-thiazolyl)thio)-8-methoxyquinoline-2-carboxylic Acid Prepared from the title compound of Example 22. mp 176°–179° C. m/e calculated for $C_{17}H_{14}N_2O_5S_2$: 390.4395. Found: 390.03114.

50. 2-((5-Carboxymethyl-4-methyl-2-thiazolyl)thio)quinoline-4-carboxylic Acid Prepared from the title compound of Example 28. mp 206°–208° C. Analysis calculated for $C_{16}H_{12}N_2O_4S_2$: C 53.32; H 3.36; N 7.77. Found: C 53.05; H 3.20; N 7.65. m/e calculated for $C_{16}H_{12}N_2O_4S_2$: 360.4130. Found: 360.02237.

51. 5-((5-Carboxymethyl-4-methyl-2-thiazolyl)thiomethyl)-thiophene-2-carboxylic Acid Prepared from the title compound of Example 27. mp 188°–190° C. Analysis calculated for $C_{12}H_{11}NO_4S_3$: C 43.75; H 3.37; N 4.25. Found: C 43.45; H 3.29; N 4.19. m/e calculated for $C_{12}H_{11}NO_4S_3$: 329.4178. Found: 328.98467.

EXAMPLE 52

2-((5-Carboxymethyl-4-methyl-2-thiazolyl)thio)-4-methyl-3-pyridinecarboxylic Acid Ethyl Ester A slurry of 642 mg (1.69 mmol) of the title compound of Example 2 in 12 ml of ethanol was treated with 68 mg of (1.69 mmol, 1.0 equivalent) of NaOH in 8 ml of water at 0° C. The mixture was stirred at 0° C. for 20 min and at room temperature for 2.5 h. The clear mixture was concentrated to remove most of the ethanol, the residue was acidified to pH 3 with 6M HCl and the resulting white precipitate was filtered to yield 500 mg (84%) of the title compound. mp 164°–166° C. $^1$H NMR (DMSO, 300 MHz): δ 1.34 (3H, t, J=7), 2.25 (3H, s), 2.36 (3H, s), 3.82 (2H, s), 4.38 (2H, q, J=7), 7.28 (1H, d, J=5), 8.45 (1H, d, J=5).

EXAMPLES 53–54

Utilizing substantially the same procedure as recited in Example 52, but substituting the appropriate starting material in place of the title compound of Example 2, the following compounds were prepared.

2-((5-Carboxymethyl-4-methyl-2-thiazolyl)thio)-6-pyridinecarboxylic Acid Ethyl Ester Prepared from the title compound of Example 6. mp 140°–142° C. Analysis calculated for $C_{14}H_{14}N_2O_4S_2$: C 49.69; H 4.17; N 8.28. Found: C 49.61; H 4.12; N 8.19. m/e calculated for $C_{14}H_{14}N_2O_4S_2$: 338.4067. Found: 338.03464.

54. 4-((5-Carboxymethyl-4-methyl-2-thiazolyl)thiomethyl)-3-pyridine carboxylic Acid Ethyl Ester Prepared from the title compound of Example 15. mp 139°–141° C. MS (m/e): 352(M$^+$), 306, 260, 136.

EXAMPLE 55

4-((5-2-Ethoxy-2-oxoethyl)-4-methyl-2-thiazolyl)thiomethyl)-3-pyridine carboxylic Acid A solution of 600 mg of the title compound of Preparation 34 in 10 ml of 30% hydrogen bromide in acetic acid soution was heated at 42°–45° C. for 3 h. The solvent was evaporated and the residue was co-evaporated with benzene to give a solid. Purification by flash chromatography using a methanol-chloroform (5:95) eluant gave 100 mg of a light yellow solid which was triturated in ether-hexane to afford 58 mg (12%) of the title compound as a light yellow solid, mp 173°–175° C. $^1$H NMR (DMSO-$d_6$): δ: 1.17 (3H, t, J=7), 2.23 (3H, s), 3.82 (2H, s), 4.07 (2H, q, J=7), 4.74 (2H, s), 7.49 (1H, d, J=7), 8.63 (1H, bd s), 8.99 (1H, bd s). MS (m/e): 352 (M$^+$), 217, 144 (base).

EXAMPLES 56–57

Utilizing substantially the same procedure as recited in Example 55, but substituting the appropriate starting material in place of the title compound of Preparation 34, the following compounds were prepared.

56. 2-((5-(2-Ethoxy-2-oxoethyl)-4-methyl-2-thiazolyl)thio)-4-methyl-3-pyridine carboxylic Acid Prepared from the title compound of Preparation 43. mp 169°–171° C. $^1$H NMR (DMSO-d$_6$): δ 1.18 (3H, t, J=7), 2.25 (3H, s), 2.39 (3H, s), 3.90 (2H, s), 4.09 (2H, q, J=7), 7.25 (1H, d, J=5), 8.41 (1H, d, J=5). Analysis calculated for $C_{15}H_{16}N_2O_4S_2$: C 51.12; H 4.58; N 7.95. Found: C 51.05; H 4.36; N 7.81. m/e calculated for $C_{15}H_{16}N_2O_4S_2$: 352.4338. Found: 352.05160.

57. 2-((5-(2-Ethoxy-2-oxoethyl)-4-methyl-2-thiazolyl)thio)-6-pyridinecarboxylic Acid Prepared from the title compound of Preparation 44. mp 123°–125° C. $^1$H NMR (DMSO-d$_6$) δ 1.20 (3H, t, J=7), 2.32 (3H, s), 3.96 (2H, s), 4.12 (2H, q, J=7), 7.47–7.96 (3H, m). FAB MS (m/e) 399 (M$^+$), 309.

EXAMPLE 58

4-((5-Carboxymethyl-4-methyl-2-thiazolyl)thio)-2-methylmercapto-1,3-pyrimidine The title compound of Example 17 (200 mg, 0.59 mmol) was dissolved in 5 ml of methanol, 5 ml of tetrahydrofuran, and 2 ml of H$_2$O under an inert atmosphere at room temperature. Freshly ground K$_2$CO$_3$ (123 mg, 0.89 mmol) was added dropwise to the methanol solution at room temperature and the reaction stirred at room temperature overnight. The reaction mixture was poured into 50 ml of H$_2$O and washed 1×50 ml Et$_2$O. The aqueous layer was acidified to pH 2 with 1N HCl and this was extracted with 3×50 ml of 9:1 Et$_2$O/THF. The combined organic layers were dried over MgSO$_4$, filtered, and stripped to an off-white solid. This was triturated with Et$_2$O to provide the title compound of this Example (134 mg, 72% yield) as a beige solid. mp 164°–165° C. m/e calcd for $C_{11}H_{11}N_3O_2S_3$: 313.4212. Found 312.99910.

EXAMPLES 59–62

Utilizing substantially the same procedure recited in Example 58, but substituting the appropriate starting material for the title compound of Example 17, the following compounds were prepared.

59. 6-((5-Carboxymethyl-4-methyl-2-thiazolyl)thio-2-methylmercaptopyrimidine-4-carboxylic Acid Prepared from the title compound of Example 18. mp 238°–239° C. Analysis calculated for $C_{12}H_{11}N_3O_4S_3$: C 40.32; H 3.10; N 11.76. Found: C 40.64; H 2.94; N 11.35. m/e calculated for $C_{12}H_{11}N_3O_4S_3$: 357.4312. Found: 356.98928.

60. 4-((5-Carboxymethyl-4-methyl-2-thiazolyl)thio)-2,6-dimethoxypyrimidine

Prepared from the title compound of Example 19. mp 164°–165° C. m/e calculated for $C_{12}H_{13}N_3O_4S_2$: 327.3831. Found: 327.03292.

61. 6-((5-(2-Methoxy-2-oxoethyl)-4-methyl-2-thiazolyl)thiomethyl)-4-hydroxy-2-methylpyrimidine Prepared from the title compound of Example 25. mp 130°–132° C. m/e calculated for $C_{13}H_{15}N_3O_3S_2$: 325.4108. Found: 325.05093.

62. 6-((5-Carboxymethyl-4-methyl-2-thiazolyl)thiomethyl)-2,4-dihydroxypyrimidine Prepared from the title compound of Example 26. mp 246°–247° C. Analysis calculated for $C_{11}H_{11}N_3O_4S_2$: C 42.16; H 3.54; N 13.41. Found: C 42.08; H 3.47; N 13.04. m/e calculated for $C_{11}H_{11}N_3O_4S_2$: 313.3560. Found: 313.01820.

EXAMPLE 63

2-((5-(2-Ethoxy-2-oxoethyl)-4-methyl-2-thiazolyl)thio)-6-trifluoromethylpyridine The title compound of Preparation 32 (100 mg, 0.264 mmol) was dissolved in 5 ml of DMF at room temperature under an inert atmosphere. Triphenylphosphine (69 mg, 0.263 mmol) was added and the reaction mixture was stirred at 160° C. overnight. After another 69 mg of triphenylphosphine (0.263 mg) was added, the reaction was stirred for an additional 3 hrs at 160° C. After removing the DMF by Kugelrohr distillation, the residue was taken up in 100 ml of Et$_2$O, poured into a separatory funnel, and washed with 4×100 ml H$_2$O. The organic layer was dried of MgSO$_4$, filtered, and the solvent stripped off. The resulting material was purified via flash chromatography (100% Et$_2$O) to provide the title compound of this Example (20 mg, 21% yield) as a yellow solid: mp 56°–57° C. Anal calcd. for $C_{14}H_{13}F_3N_2O_2S_2$: C 46.40; H 3.62; N 7.73. Found: C 46.12; H 3.39; N 7.43. m/e calculated for $C_{14}H_{13}F_3N_2O_2S_2$: 362.3951. Found: 362.03815.

EXAMPLE 64

4-((5-(2-Ethoxy-1-ethyl-2-oxoethyl)-4-methyl-2-thiazolyl)thio)-3-pyridinecarboxylic Acid Ethyl Ester Sodium hydride (1.55 g, 38.8 mmol, 60% dispersion in oil) was washed with hexanes and suspended in N,N-dimethylformamide (100 ml). The suspension was cooled to 0° C. in an ice bath and the title compound of Preparation 37 (11.9 g, 35.2 mmol) was added, as a solution in N,N-dimethylformamide (40 ml), in portions over five minutes. The reaction mixture was warmed to room temperature and iodoethane (3.09 ml, 38.6 mmol) was added via syringe at a steady rate. The reaction mixture was stirred at room temperature for one hour at which time another portion of sodium hydride (650 mg) was added. The reaction mixture was heated at 75° C. for one hour then another portion of iodoethane (2 ml) was added. The reaction mixture was stirred at 100° C. for one hour and then at room temperature for 16 hours. The reaction mixture was quenched with water (15 ml) and then partitioned between water (700 ml) and diethyl ether (500 ml). The layers were separated and the ether layer was washed with saturated aqueous NaHCO$_3$ and saturated aqueous NaCl. The original aqueous layer was extracted an additional two times with diethyl ether (700 ml each). The organic layers were combined and dried (MgSO$_4$), filtered and the solvent was removed in vacuo. The title compound of this Example was isolated by flash chromatography (20% hexanes/Et$_2$O followed by 100% Et$_2$O) to afford a yellow oil. This oil was further flash chromatographed (50% CH$_2$Cl$_2$/Et$_2$O followed by 100% Et$_2$O) to afford a yellow oil. Anal. calcd. for $C_{18}H_{22}N_2O_4S_2$: C 54.80; H 5.62; N 7.10. Found: C 54.86; H 5.22; N 6.82.

Preparation 1

2-Chloro-3-pyridinecarboxylic Acid 1-Oxide Ethyl Ester

A solution of m-chloroperbenzoic acid (mCPBA), prepared by suspending 41.4 g (0.021 mol) of 50% mCPBA in 100 ml of dichloromethane, adding a drying agent (sodium sulfate), and removing the solids by filtration, was added dropwise to a solution of 22.2 g (0.12 mol) of 2-chloro-3-pyridinecarboxylic acid ethyl ester (Aldrich, 1001 West Saint Paul Avenue, Milwaukee, Wis. 53233 USA) in 100 ml of dichloromethane. After stirring the mixture for 36 hours, the precipitate was removed by filtration and the filtrate was evaporated. The residue was dissolved in ethyl acetate, washed successively with saturated aqueous sodium bisulfite solution (1×100 ml) and sodium bicarbonate solution (2×100 ml), dried ($Na_2SO_4$), and evaporated. The residue was purified by flash chromatography with an ethyl acetate-hexane eluant (5:95 to 100:0) to afford 8.1 g (33%) of the title compound as an oil. $^1H$ NMR ($CDCl_3$): δ 1.35 (3H, t, J=7), 4.36 (2H, q, J=7), 7.23–7.29 (1H, m), 7.61 (1H, d, J=7), 8.41 (1H, d, J=7).

Preparations 2–8

Utilizing substantially the same procedure as recited in Preparation 1, but substituting the appropriate starting material for 2-chloro-3-pyridinecarboxylic acid ethyl ester, the following compounds were prepared.

2. 2-Chloro-4-pyridinecarboxylic Acid 1-Oxide Methyl Ester

Prepared from 2-chloro-4-pyridinecarboxylic acid methyl ester (for preparation, see Adger et al., J. Chem. Soc. Perkin Trans. I, 1988, 2785). mp 121°–123° C. $^1H$ NMR ($CDCl_3$, 300 MHz): δ 3.92 (3H, s), 7.77 (1H, dd, J=7, 2), 8.08 (1 H, d, J=2), 8.32 (1H, d, J=7).

3. 2-Bromo-5-methyl-3-pyridinecarboxylic Acid 1-Oxide Ethyl Ester

Prepared from 2-bromo-5-methyl-3-pyridinecarboxylic acid ethyl ester (for preparation, see Baldwin et al., Journal of Organic Chemistry, 1978, 43, 2529). mp 107°–108° C. $^1H$ NMR ($CDCl_3$): δ 1.42 (3H, t, J=7), 2.32 (3H, s), 4.43 (2H, q, J=7), 7.34 (1H, s), 8.30 (1H, s).

4. 2-Bromo-4-methyl-3-pyridinecarboxylic Acid 1-Oxide Ethyl Ester

Prepared from 2-bromo-4-methyl-3-pyridinecarboxylic acid ethyl ester (for preparation, see Baldwin et al., Journal of Organic Chemistry, 1978, 43, 2529). $^1H$ NMR ($CDCl_3$): δ 1.39 (3H, t, J=7), 2.29 (3H, s), 4.43 (2H, q, J=7), 7.07 (1H, d, J=7), 8.26 (1H, d, J=7).

5. 2-Chloro-6-methyl-3-pyridinecarboxylic Acid 1-Oxide Ethyl Ester

Prepared from 2-chloro-6-methyl-3-pyridinecarboxylic acid ethyl ester (for preparation, see Morris et al., Journal of the Chemical Society, 1963, 1841). $^1H$ NMR ($CDCl_3$): δ 1.33 (3H, t, J=7), 2.51 (3H, s), 4.33 (2H, q, J=7), 7.10 (1H, d, J=8), 8.00 (1H, d, J=8).

6. 2-Chloro-3-pyridineacetic Acid 1-Oxide Ethyl Ester

Prepared from the title compound of Preparation 13 hereinbelow. $^1H$ NMR ($CDCl_3$): δ 1.22 (3H, t, J=8), 3.75 (2H, s), 4.14 (2H, q, J=8), 7.10–7.20 (1H, m), 8.27 (1H, dd, J=8).

7. 4-Methyl-3-pyridinecarboxylic Acid 1-Oxide Benzyl Ester

Prepared from the title compound of Preparation 40, hereinbelow. mp 123°–125° C. $^1H$ NMR ($CDCl_3$): δ 2.57 (3H, s), 5.31 (2H, s), 7.13 (1H, d, J=7), 7.28–7.40 (5H, m), 8.15 (1H, d, J=7), 8.72 (1H, s). MS (m/e): 243 ($M^+$), 181, 91 (base).

8. 2-Bromo-4-Methyl-3-pyridinecarboxylic Acid 1-Oxide Benzyl Ester

Prepared from the title compound of Preparation 41. $^1H$ NMR ($CDCl_3$): δ 2.22 (3H, s), 5.38 (2H, s), 7.04 (1H, d, J=7), 7.35–7.42 (5H, m), 8.25 (1H, d, J=7). MS (m/e): 323, 321 ($M^+$), 198, 200, 91 (base).

Preparation 9

6-Chloro-2-pyridinecarboxylic Acid 1-Oxide

To a solution of 6-chloro-2-pyridinecarboxylic acid (14.8 g, 0.093 mol, for preparation, see Delarge, II. Farmaco-Ed.Sc., 1967, 22, 1069) in trifluoroacetic acid (110 ml) was added 75 ml of 30% aqueous hydrogen peroxide solution. The mixture was heated to 60° for 2 hours, cooled to room temperature and poured onto ice water. The white precipitate was filtered and was washed well with water to yield 10.8 g (67%) of the title compound of this preparation. mp 168°–170° C. $^1H$ NMR ($CDCl_3$): δ 7.46 (1H, d, J=8), 7.77 (1H, dd, J=8, 8), 8.01 (1H, d, J=8).

Preparations 10–12

Utilizing substantially the same procedure as recited in Preparation 9, but substituting the appropriate starting material for 6-chloro-2-pyridine carboxylic acid, the following compounds were prepared.

10. 2-Chloro-3-trifluoromethyl pyridine-1-oxide

Prepared from 2-chloro-3-trifluoromethyl pyridine (Fluorochem Limited, Wesley St., Old Glossop, Derbyshire SK13 9RY, United Kingdom). mp 97°–98° C. Anal. calcd. for $C_6H_3ClF_3NO$: C 36.48; H 1.53; N 7.09. Found: C 36.13; H 1.34; N 6.88. m/e calcd. for $C_6H_3ClF_3NO$: 197.5451. Found: 196.98306.

11. 2-Chloro-4-trifluoromethyl pyridine-1-oxide

Prepared from 2-chloro-4-trifluoromethyl pyridine (Fluorochem Limited, Wesley St., Old Glossop, Derbyshire SK13 9RY, United Kingdom). mp 44°–46°.

12. 2-Chloro-6-trifluoromethyl pyridine-1-oxide

Prepared from 2-chloro-6-trifluoromethyl pyridine (Fluorochem United, Wesley St., Old Glossop, Derbyshire SK13 9RY, United Kingdom). $^1H$ NMR ($DMSO-d_6$): δ 8.14 (1H, dd, J=10, 2), 7.99 (1H, dd, J=8, 2), 7.52 (1H, dd, J=10, 8).

Preparation 13

2-Chloro-3-pyridineacetic Acid Ethyl Ester

A mixture of 1.56 g (8.6 mol) of 3-pyridineacetic acid ethyl ester 1-oxide (for preparation, see A. R. Katritzky, J. Chem. Soc., 1956, 2404) and 15 ml of phosphorous oxychloride was heated to 80° C. for 3 hours. After cooling, the solvent was evaporated and the residue was poured onto ice water and solid sodium bicarbonate was added until the pH was basic. The organic layer was extracted with ethyl acetate and the combined extracts were dried over sodium sulfate and evaporated to an oil which was purified by flash chromatography with an ethyl acetate-hexane (1:4–1:1) eluant.

The fractions containing the less polar isomer (Rf 0.3, ethyl acetate-hexane (3:7)) were combined and evaporated to yield 584 mg (50%) of the title compound of this preparation as an oil. $^1$H NMR (CDCl$_3$): δ 1.22 (3H, t, J=7), 3.76 (2H, s), 4.15 (2H, q, J=7), 7.11–7.21 (2H, m), 8.25–8.31 (1H, m).

Preparation 14

Ethyl 4-chloro-8-methoxy-2-quinoline carboxylate

Prepared from ethyl 4-hydroxy-8-methoxy-2-quinoline carboxylate (Bader, 1001 West Saint Paul Avenue, Milwaukee, Wis., 53233 USA) utilizing the same procedure as cited in Preparation 13. mp 131°–132°. m/e calcd for C$_{13}$H$_{12}$ClNO$_3$: 265.6985. Found: 265.05245.

Preparation 15

6-Chloro-2-pyridinecarboxylic Acid 1-Oxide Ethyl Ester

A slurry of the title compound of Preparation 9 (9.0 g, 0.051 mol) in absolute ethanol (200 ml) was chilled to 0° C. and was saturated with hydrogen chloride gas. After refluxing for 3 hours, the mixture was evaporated. The residue was dissolved in ethyl acetate, washed with saturated aqueous sodium bicarbonate, dried (Na$_2$SO$_4$) and evaporated to afford 4.27 g (41%) of the title compound of this Preparation. $^1$H NMR (CDCl$_3$): δ 1.28 (3H, t, J=7), 4.35 (2H, q, J=7), 7.19 (1H, t, J=8), 7.40 (1H, d, J=8), 7.52 (1H, d, J=8).

Preparation 16

Methyl-4-chloroquinaldate

4-Chloroquinaldic acid (the title compound of Preparation 22 hereinbelow) (1.5 g, 7.22 mmol) was dissolved in 50 ml of DMF at room temperature under an inert atmosphere. This solution was cooled to 0°, whereupon NaH (60% dispersion in oil, 434 mg, 10.8 mmol) was added in one portion. After stirring the reaction mixture for 5 minutes at 0° C., CH$_3$I (0.68 ml, 10.9 mmol) was added via syringe. The ice bath was removed after 1 hr, and the reaction mixture stirred at room temperature overnight. The reaction mixture was poured into a separatory funnel with 50 ml H$_2$O. This was then extracted 3×100 ml CH$_2$Cl$_2$. The combined organics were dried over MgSO$_4$, filtered, and stripped to provide the title compound of this Preparation (1.6 g, 100% yield) as a white solid. $^1$H NMR (CDCl$_3$): δ 8.34–8.27 (2H, multiplet), 7.85 (1H, ddd, J=9, 7, 1), 7.78 (1H, ddd, J=9, 7, 1), 7.26 (1H, s), 4.09 (3H, s).

Preparation 17

Methyl 2-chloroquinoline-4-carboxylate

Utilizing substantially the same procedure as recited in Preparation 16, but substituting 4-carboxy-2-chloroquinoline (Bader, 1001 West Saint Paul Avenue, Milwaukee, Wis., 53233 USA) for 4-chloroquinaldic acid, the title compound of this Preparation was prepared. $^1$H NMR (DMSO-d$_6$): δ 8.56 (1H, d, J=7), 8.05 (1H, d, J=7), 7.94 (1H, s), 7.92 (1H, ddd, J=9,7,1), 7.78 (1H, ddd, J=9,7,1), 4.00 (3H, s).

Preparation 18

3-(2-Ethoxy-2-oxoethyl)-2-trifluoromethanesulfonyl-1,4-quinoxaline 3-(2-Ethoxy-2-oxoethyl)-2-hydroxy-1,4-quinoxaline (1.0 g, 4.31 mmol, Aldrich, 1001 West Saint Paul Avenue, Milwaukee, Wis. 53233 USA) and 4-dimethylaminopyridine (527 mg, 4.31 mmol) were combined in 20 ml CH$_2$Cl$_2$ and 1.2 ml triethylamine at room temperature under an inert atmosphere. The reaction mixture was cooled to −78° and trifluoromethanesulfonic anhydride (0.77 ml, 4.58 mmol) was added dropwise via syringe. The ice bath was removed and the reaction allowed to warm to 0° and then stirred at that temperature overnight. After cooling back to −78° and adding an additional 0.4 ml of trifluoromethanesulfonic anhydride (2.4 mmol), the reaction mixture was allowed to warm to room temperature and stirred for an additional 1½ hrs. The reaction mixture was poured into 75 ml H$_2$O, the layers were separated, and the aqueous layer was extracted 2×50 ml CH$_2$Cl$_2$. The combined organics were dried over MgSO$_4$, filtered, and stripped of solvents The resulting dark brown oil was purified via flash chromatography (1:1 Et$_2$O/hexane) to provide the title compound of this Preparation (862 mg, 55% yield) as a yellow oil. $^1$H NMR (DMSO-d$_6$): δ 8.19 (1H, dd, J=7, 3), 8.08 (1H, dd, J=7, 3), 4.24 (2H, s), 4.14 (2H, quart, J=7), 1.18 (3H, t, J=7).

Preparation 19

Methyl 5-methyl-2-thiophene carboxylate

5-Methyl-2-thiophene carboxylate (2.0 g, 14.1 mmol, Aldrich, 1001 West Saint Paul Avenue, Milwaukee, Wis. 53233 USA) was carefully dissolved in 50 ml methanol and 15 ml conc. sulfuric acid at room temperature under an inert atmosphere. The reaction mixture was refluxed at 83° C. for 5 hours. After the reaction mixture was allowed to cool to room temperature, it was poured into a beaker containing 200 ml of ice. This aqueous mixture was neutralized to pH 7 with solid NaHCO$_3$. This liquid was poured into a separatory funnel and extracted 2×200 ml CH$_2$Cl$_2$. The combined organics were dried over MgSO$_4$, filtered, and stripped to provide the title compound of this Preparation (2.2 g, 67% yield) as a brown oil. $^1$H NMR (CDCl$_3$): δ 7.61 (1H, d J=4), 6.77 (1H, d, J=4), 3.84 (3H, s), 2.52 (3H, s).

Preparation 20

Methyl 5-(bromomethyl)-2-thiophene carboxylate

The title compound of Preparation 19 (1.9 g, 12.2 mmol), N-bromosuccinimide (NBS, 2.2 g, 12.4 mmol), and benzoyl peroxide (20 mg, 0.08 mmol) were combined with 125 ml CCl$_4$ under an inert atmosphere at room temperature. The reaction mixture was heated to 87° for 4 hrs. An additional 540 mg of NBS (3.0 mmol) and 75 mg of benzoyl peroxide (0.3 mmol) were then added and the reaction mixture was stirred for another hour at 87°. The reaction mixture was filtered while hot and the filtrate was stripped to provide the title compound of this Preparation (811 mg, 28% yield) as a brown oil. $^1$H NMR (CDCl$_3$): δ 7.63 (1H, d, J=4), 7.09 (1H, d, J=4), 4.68 (2H, s), 3.89 (3H, s).

Preparation 21

4-Chloroquinaldehyde

4-Chloroquinaldine (10 ml 49.6 mmol, Aldrich, 1001 West Saint Paul Avenue, Milwaukee, Wis. 53233 USA) and 8.26 g of selenium dioxide (74.4 mmol) were dissolved in 10 ml of acetic acid and 660 ml of t-butyl alcohol at room temperature under an inert atmosphere. The reaction mixture was heated to 100° for 4 hrs., whereupon it was allowed to cool to room temperature. The reaction material was filtered through a pad of Celite, rinsing with EtOAc. The filtrate was poured into a separatory funnel and washed with 1×500 ml saturated bicarbonate solution, 1×500 ml saturated NH$_4$Cl solution, 1×500 ml NH$_4$OH, 1×500 ml 1N HCl, 1×500 ml saturated bicarbonate solution, and 1×50 ml H$_2$O. The organic layer was dried over MgSO$_4$, filtered and the solvent stripped off. The resulting material was purified via flash chromatography (1:1 CH$_2$Cl$_2$/hexane) to provide the title compound of this Preparation (2.3 g., 24% yield) as a yellow oil.

Preparation 22

4-Chloroquinaldic acid

Silver oxide was prepared by adding a solution of AgNO$_3$ (7.8 g, 45.9 mmol) in 20 ml of H$_2$O to a solution of NaOH (3.67 g, 91.9 mmol) in 20 ml H$_2$O to form a brown semi-solid under an inert atmosphere. This was cooled on ice and a solution of the title compound of Preparation 21 (4.4 g, 23.0 mmol) in 2 ml of EtOH was added. The ice bath was removed after 2 minutes and the reaction mixture was stirred for 3.5 hours at room temperature. The reaction mixture was then filtered and rinsed with 3×50 ml hot H$_2$O. The filtrate was allowed to cool to room temperature and then poured into a separatory funnel. After extracting 3×100 ml CH$_2$Cl$_2$, the combined organic layers were dried over MgSO$_4$, filtered, and stripped to a solid. This was taken up In 50 ml 2N HCl, and heated to 50° C. for 2 hours. The salts were filtered off and the filtrate was extracted 3×100 ml CH$_2$Cl$_2$. The combined organics were dried over MgSO$_4$. This HCl heating/CH$_2$Cl$_2$ extraction treatment was repeated twice more. The solvent was stripped off the final time to provide the title compound of this Preparation (2.04 g, 43% yield) as a white solid. $^1$H NMR (CDCl$_3$): δ 8.35 (1H, dd, J=9, 1), 8.20 (1H, dd, J=9, 1), 7.92 (1H, ddd, J=9, 7, 1), 7.85 (1H, ddd, J=9, 7, 1), 7.26 (1H, s).

Preparation 23

2-((5-(2-Ethoxy-2-oxoethyl)-4-methyl-2-thiazolyl) thio)-3-pyridinecarboxylic Acid Ethyl Ester 1-Oxide A mixture of 4.73 g (0.022 mol) of 5-(2-ethoxy-2-oxoethyl)-2-mercapto-4-methyl-1,3-thiazole (K. Fleishmann, K. H. Scheunemann, H. U. Schorlemmer, G. Dickneite, J. Blumbach, G. F. Fischer, W. Durckheimer and H. H. Sedlacek, Arzneim.-Forsch./Drug Res., 1989, 39 (II), 743), 4.0 g (0.02 mol) of the title compound of Preparation 1, 5.40 g (0.039 mol) of anhydrous potassium carbonate, and 100 ml of acetone was heated to reflux. Aliquots were taken periodically and assayed by tlc for the consumption of the chloropyridine starting material. After 3 hours, the mixture was cooled and the solvent was removed by rotary evaporation. The residue was partitioned between ethyl acetate and water, and the organic layer was separated and washed with two additional portions of water. Drying (Na$_2$SO$_4$), evaporation, and purification of the residue by flash chromatography with an ethyl acetate-hexane (1:1) eluant afforded 7.40 g (97%) of the title compound of this preparation as an oil. $^1$H NMR (CDCl$_3$): δ 1.23 (3H, t, J=7), 1.29 (3H, t, J=7), 2.26 (3H, s), 3.67 (2H, s), 4.08–4.19 (4H, m), 7.22–7.28 (1H, m), 7.53 (1H, d, J=8), 8.27 (1H, d, J=7).

Preparations 24–36

Utilizing substantially the same procedure as recited in Preparation 23, but substituting the appropriate starting material for the title compound of Preparation 1, the following compounds were prepared.

24. 2-((5-(2-Ethoxy-2-oxoethyl)-4-methyl-2-thiazolyl)thio)-4-pyridinecarboxylic Acid Methyl Ester 1-Oxide Prepared from the title compound of Preparation 2. mp 112°–114° C. $^1$H NMR (CDCl$_3$): δ 1.24 (3H, t, J=7), 2.42 (3H, s), 3.78 (2H, s), 3.82 (3H, s), 4.16 (2H, q, J=7), 7.57 (1H, d, J=2), 7.62 (1H, dd, J=7, 2), 8.19 (1H, d, J=7).

25. 2-((5-(2-Ethoxy-2-oxoethyl)-4-methyl-2-thiazolyl)thio)-5-methyl-3-pyridinecarboxylic Acid Ethyl Ester 1-Oxide Prepared from the title compound of Preparation 3. $^1$H NMR (CDCl$_3$): δ 1.22 (3H, t, J=7), 1.30 (3H, t, J=7), 2.25 (3H, s), 2.30 (3H, s), 3.65 (2H, s), 4.13 (2H, q, J=7), 4.19 (2H, q, J=7), 7.33 (1H, s), 8.12 (1H, s).

26. 2-((5-(2-Ethoxy-2-oxoethyl)-4-methyl-2-thiazolyl)thio)-4-methyl-3-pyridinecarboxylic Acid Ethyl Ester 1-Oxide Prepared from the title compound of Preparation 4. $^1$H NMR (CDCl$_3$): δ 1.23 (3H, t, J=7), 1.32 (3H, t, J=7), 2.29 (3H, s), 3.64 (2H, s), 4.13 (2H, q, J=7), 4.36 (2H, q, J=7), 7.10 (1H, d, J=7), 8.18 (1H, d, J=7).

27. 2-((5-(2-Ethoxy-2-oxoethyl)-4-methyl-2-thiazolyl)thio)-6-methyl-3-pyridinecarboxylic Acid Ethyl Ester 1-Oxide Prepared from the title compound of Preparation 5. $^1$H NMR (CDCl$_3$): δ 1.24 (3H, t, J=7), 1.27 (3H, t, J=7), 2.26 (3H, s), 2.50 (3H, s), 3.66 (2H, s), 4.11 (2H, q, J=7), 4.14 (2H, q, J=7), 7.22 (1H, d, J=8), 7.45 (1H, d, J=8).

28. 4-Methyl-2-(2-pyridinylthio)-5-thiazoleacetic Acid Ethyl Ester 1-Oxide

Prepared from 2-bromopyridine-1-oxide (for preparation, see Shaw, et al., J. Org. Chem., 1950, 72, 4362). $^1$H NMR (CDCl$_3$): δ 1.20 (3H, t, J=7), 2.38 (3H, s), 3.75 (2H, s), 4.10 (2H, q, J=7), 6.82 (1H, dd, J=7, 1), 6.96–7.08 (1H, m), 8.49 (1H, d, J=7).

29. 2-((5-(2-Ethoxy-2-oxoethyl)-4-methyl-2-thiazolyl)thio)-3-pyridineacetic Acid Ethyl Ester 1-Oxide Prepared from the title compound of Preparation 6. $^1$H NMR (CDCl$_3$): δ 1.16–1.20 (6H, m), 2.26 (3H, s), 3.62 (2H, s), 3.97 (2H, s), 4.03–4.13 (4H, m), 7.10–7.31 (2H, m), 8.22 (1H, d, J=6).

30. 2-((5-(2-Ethoxy-2-oxoethyl)-4-methyl-2-thiazolyl)thio)-4-trifluoromethyl pyridine-1-oxide Prepared from the title compound of Preparation 10. Anal. calcd. for C$_{14}$H$_{13}$N$_2$O$_3$S$_2$F$_3$: C 44.44; H 3.46; N 7.40. Found: C 44.49; H 3.28; N 7.51.

31. 2-((5-(2-Ethoxy-2-oxoethyl)-4-methyl-2-thiazolyl)thio)-4-trifluoromethyl pyridine-1-oxide Prepared from the title compound of Preparation 11. mp 97°–99° C.

32. 2-((5-(2-Ethoxy-2-oxoethyl)-4-methyl-2-thiazolyl)thio)-6-trifluoromethyl pyridine-1-oxide Prepared from the title compound of Preparation 12. mp 94°–96° C.

33. 6-((5-(Ethoxy-2-oxoethyl)-4-methyl-2-thiazolyl) thio-2-pyridinecarboxylic Acid 1-Oxide Ethyl Ester Prepared from the title compound of Preparation 15. $^1$H NMR (CDCl$_3$): δ 1.25 (3H, t, J=7), 1.38 (3H, t, J=7), 2.42 (3H, s), 3.78 (2H, s), 4.17 (2H, q, J=7), 4.42 (2H, q, J=7), 6.99 (1H, dd, J=8, 2), 7.11 (1H, t, J=8), 7.38 (1H, dd, J=8, 2).

34. 4-((5-(2-Ethoxy-2-oxoethyl)-4-methyl-2-thiazolyl)thiomethyl)-3-pyridinecarboxylic Acid Benzyl Ester Prepared from the title compound of Preparation 39 hereinbelow. $^1$H NMR (CDCl$_3$): δ 1.23 (3H, t, J=7), 2.29 (3H, s), 3.62 (2H, s), 4.14 (2H, q, J=7), 4.71 (2H, s), 5.38 (2H, s), 7.35–7.43 (6H, m), 8.57 (1H, d, J=5), 9.15 (1H, s). FAB MS (m/e): 443 (M$^+$+1).

35. 2-((5-2-Ethoxy-2-oxoethyl)-4-methyl-2-thiazolyl)thio)-4-methyl-3-pyridinecarboxylic Acid 1-Oxide Benzyl Ester Prepared from the title compound of Preparation 8 hereinabove. $^1$H NMR (CDCl$_3$): δ 1.23 (3H, t, J=7), 2.21 (3H, s), 2.29 (3H, s), 3.63 (2H, s), 4.12 (2H, q, J=7), 5.30 (2H, s), 7.07 (1H, d, J=7), 7.30–7.37 (5H, m), 8.12 (1H, d, J=7). MS (m/e): 458 (M$^+$), 422, 128, 91.

36. 2-((5-(2-Ethoxy-2-oxoethyl)-4-methyl-2-thiazolyl)thio)-6-pyridinecarboxylic Acid 1-Oxide Benzyl Ester Prepared from the title compound of Preparation 42 hereinbelow. $^1$H NMR (CDCl$_3$): δ 1.27 (3H, t, J=7), 2.44 (3H, s), 3.78 (2H, s), 4.20 (2H, q, J=7), 5.48 (2H, s), 6.96–7.41 (8H, m).

Preparation 37

4-((5-(2-Ethoxy-2-oxoethyl)-4-methyl-2-thiazolyl) thio)-3-pyridinecarboxyic Acid

A. 3-Methyl-4-nitro-pyridine-N-oxide

3-Methyl pyridine-N-oxide (171.1 g, 1.57 moles, Aldrich) was added slowly (over 10 minutes) to ice-cold (0° C.) sulfuric acid (325 ml). After addition was complete the ice-bath was removed and potassium nitrate (301 g) was added in small portions over ten minutes. After addition was complete the reaction mixture was heated at 98° C. for four hours and then poured onto crushed ice (1000 ml). The solid precipitate was filtered off and the filtrate was adjusted to pH 6 by cooling to 0° C. and adding concentrated NaOH dropwise. A yellow solid precipitated. This was filtered, suspended in 50% EtOAc/(CH$_3$)$_2$CO (800 ml), heated and filtered. The trituration was repeated twice with 300 ml of EtOAc/(CH$_3$)$_2$CO. The filtrates were evaporated in vacuo to afford a yellow solid which was recrystallized from acetone to afford 47.8 g of the title compound of part A. mp 135°–137° C. More material was obtained by extracting the aqueous filtrate from the first filtration with CH$_2$Cl$_2$ (2×400 ml), combining and drying over MgSO$_4$. The solvent was removed via rotary evaporation and the residue was combined with the filtrate from the recrystallization and then triturated with 50% EtOAc/(CH$_3$)$_2$CO as before. Recrystallization afforded 29.8 g of the title compound of Part A (mp 135°–138° C.). The filtrate from the second recrystallization afforded another 17.96 g of title compound after standing overnight at room temperature (mp 135°–137° C.).

B. 4-Nitro-3-pyridinecarboxylic acid N-oxide

Sodium dichromate (138.6 g, 465 mmol) was added portionwise over 10 minutes to a cooled (NaCl/ice) flask containing sulfuric acid (175 ml). A solution of the title compound of Part A of this preparation (47.81 g, 310 mmol) in sulfuric acid (175 ml) was prepared by adding the title compound of Part A to a cooled (0° C.) flask containing sulfuric acid. This solution was added dropwise over 45 minutes to the cooled dichromate/H$_2$SO$_4$ suspension, keeping the temperature between 20°–30° C. The temperature was kept at 20° C. for 0.5 hour after addition was complete and then at 45°–50° C. for 3 hours. The reaction mixture was cooled to room temperature and poured onto 1500 ml of ice and filtered. The filter cake was washed with water, ethanol and tetrahydrofuran. The filtrate was extracted with 80% EtOAc/THF, dried over MgSO$_4$ and the solvent was removed via rotary evaporation. The residue was combined with the original filter cake and was dissolved in 30% ammonium hydroxide (aq., 480 ml) and filtered. The filter cake was washed with more 30% ammonium hydroxide followed by H$_2$O. The filtrate was cooled and acidified with 20% aqueous HCl and cooled in refrigerator overnight. A beige precipitate was filtered off, washed with H$_2$O (50 ml), EtOAc (50 ml) and THF (50 ml). The solid was dried to afford 60.29 g of the title compound of Part B. The filtrate was extracted with 80% EtOAc/THF, dried over MgSO$_4$ and the solvent was removed via rotoary evaporation to afford an additional 23.1 g of title compound. mp. 175°–179° C.

C. 4-Chloro-3-pyridinecarboxylic acid N-oxide

Acetyl chloride (250 ml) was cooled to 0° C. and the title compound of Part B of this preparation (60.29 g, 327.5 mmol) was added in several portions. After addition was complete the ice bath was removed and the reaction mixture was heated to 70° C. for 2.5 hours. The reaction mixture was cooled to room temperature and the acetyl chloride was removed in vacuo. The residue was dissolved in toluene (200 ml) and the toluene was removed in vacuo to azeotrope the acetyl chloride. The residue was azeotroped with toluene once more and was then slurried in methanol (100 ml) and filtered. The filter cake was washed with 40 ml of methanol and then with 50 ml of toluene to afford 25.2 g of white solid 4-chloro-3-pyridinecarboxylic acid N-oxide. mp 181°–182° C. The filtrate was concentrated in vacuo and the residue was triturated with 5% methanol/toluene, filtered and the solid filter cake was dissolved in aqueous NaOH, acidified with 20% HCl, filtered and washed with water to afford, after drying in vacuo, an additional 26 g of 4-chloro-3-pyridinecarboxylic acid N-oxide. mp. 179°–180° C.

D. 2-Trimethylsilylethyl 4-chloro-3-pyridinecarboxylate N-oxide

The title compound of Part C of this preparation (51.29 g, 295.5 mmol), pyridine (46.0 ml, 568.7 mmol) and 2-(trimethylsilyl)ethanol (51.3 ml, 357.9 mmol) were dissolved in acetonitrile (820 ml) and N,N-dimethylformamide (DMF, 1600 ml). The reaction mixture was cooled to 0° C. and a solution of 1,3-dicyclohexylcarbodiimide (67.2 g, 325.7 mmol) in N,N-dimethylformamide (100 ml) was added dropwise at a rapid rate from an addition funnel over ten minutes. The addition funnel was rinsed with DMF (10 ml) and the reaction mixture was warmed slowly to room temperature and then stirred at room temperature for 16 hours. The reaction mixture was filtered and the filtrate was concentrated to approximately 100–200 ml in vacuo. The residue was flash chromatographed (5% methanol/47.5%

Et₂O/47.5% CH₂Cl₂) to obtain a foamy solid which was recrystallized from 50% ether/hexanes to afford 26.19 g of the title compound of Part D. After collection of 2nd and 3rd crops the total yield was 49.35 g (61%) mp 74°–75° C.

E. 2-Trimethylsilylethyl 4-((5-(2-oxy-2-oxoethyl)-4-methyl-2-thiazolyl)thio)-3-pyridinecarboxylate N-Oxide The title compound of Part D of this preparation (49.35 g, 180.25 mmol) was dissolved in acetone (2000 ml) and 5-(2-ethoxycarbonylethyl)-2-mercapto-4-methyl-1,3-thiazole (see Preparation 23, 43.09 g, 198.3 mmol) was added. Finely ground $K_2CO_3$ (27.41 g, 198 mmol) was added and the reaction mixture was stirred at room temperature for 16 hours. Another portion of $K_2CO_3$ (14.0 g) and 5-(2-ethoxycarbonylethyl)-2-mercapto-4-methyl-1,3-thiazole (8.0 g) was added and the reaction mixture was heated to 70° C. for five hours. The reaction mixture was cooled and stirred for 16 hours at room temperature. The reaction mixture was filtered and the filter cake was washed with acetone. The solvent was removed from the filtrate in vacuo and the residue was partitioned between saturated aqueous $NaHCO_3$ (800 ml) and 90% diethyl ether/THF (900 ml). The layers were separated and the organic layer was washed with aqueous NaCl solution (800 ml). The aqueous layer was extracted with 2 portions of 90% Et₂O/THF (500 ml). The combined organic layers were dried ($MgSO_4$), filtered and the solvents were removed in vacuo to afford a brown oil which was flash chromatographed (5% MeOH/47.5% Et₂O/47.5% CH₂Cl₂) followed by 30% MeOH/Et₂O to afford 67.63 g of the title compound of Part E as a brown oil.

F. 2-Trimethylsilylethyl 4-((5-(2-ethoxy-2-oxoethyl)-4-methyl-2-thiazolyl)thio)-3-pyridinecarboxylate The title compound of Part E of this preparation (67.63 g, 149 mmol) was dissolved in CH₂Cl₂ (2000 ml) at room temperature. The reaction mixture was treated dropwise with phosphorous trichloride (2.0M in CH₂Cl₂, 75.7 ml, 151.4 mmol). The reaction mixture was stirred at room temperature for 16 hours. One half of the reaction mixture was poured into aqueous $NaHCO_3$ (800 ml) and the organic layer was separated. The organic layer was washed with aqueous NaCl (800 ml) and the aqueous layers were again extracted with CH₂Cl₂ (200 ml). The other half of the reaction mixture was worked up in similar fashion and the organic layers were combined, dried ($MgSO_4$), filtered and the solvents were removed in vacuo to afford 57.23 g of the title compound of Part F as a brown oil.

G. 4-((5-(2-Ethoxy-2-oxoethyl)-4-methyl-2-thiazolyl)thio)-3-pyridinecarboxylic acid The title compound of Part F of this preparation (50 g, 114 mmol) was dissolved in tetrahydrofuran (330 ml) and treated dropwise over twenty minutes with tetra-n-butylammonium fluoride (1.0M in THF, 138 ml, 130 mmol) and was stirred at room temperature for 16 hours. The reaction mixture was quenched with H₂O (200 ml) and then concentrated in vacuo. The residue was partitioned between 0.5N NaOH (300 ml) and Et₂O (300 ml) and the layers were separated. The aqueous layer was washed with another portion of Et₂O (300 ml) and then acidified to pH 1. A beige precipitate formed which was filtered, wash with cold H₂O (25 ml) and dried. The aqeuous layer was extracted with 75% Et₂O/THF (3×300 ml) and dried ($MgSO_4$), filtered and the solvents were removed in vacuo. The residue combined with the filter cake and was flash chromatographed (2% triethylamine/10% MeOH/88% CH₂Cl₂) to afford 11.9 g of the title compound of this preparation as a brown oil. ¹H NMR (DMSO-d₆): 9.00 (1H, s), 8.49 (1H, d, J=6), 6.76 (1H, d, J=6), 4.13 (2H, q, J=7), 4.04 (2H, s), 2.38 (3H, s), 1.21 (3H, t, J=7). Analysis calculated for $C_{14}H_{14}N_2O_4S_2$: C 49.69; H 4.17; N 8.28. Found: C 49.47; H 4.02; N 8.06. m/e calculated for $C_{14}H_{14}N_2O_4S_2$: 338.4067. Found: 338.04531.

Preparation 38

2-Chloro-5-pyridinecarboxylic Acid Methyl Ester

To a slurry of 2.0 g of 6-chloro-3-pyridinecarboxylic acid (Aldrich, 1001 West Saint Paul Avenue, Milwaukee, Wis. 53233 USA) in methanol (200 ml) was added two drops of concentrated aqueous hydrochloric acid and the mixture was stirred overnight at room temperature. The solvent was evaporated and the residue was dissolved in ethyl acetate, washed with saturated aqueous sodium bicarbonate solution, dried over sodium sulfate, and evaporated to give 1.5 g (71%) of product as a white solid. mp 90°–92° C.

Preparation 39

4-Chloromethyl-3-pyridinecarboxylic Acid Benzyl Ester Hydrochloride

A mixture of the title compound of Preparation 7 (1.8 g, 7.3 mmol), p-toluenesulfonylchloride (2.0 g, 11 mmol) and dioxane (10 ml) was heated under reflux for 1.5 hours. The reaction mixutre was cooled to 0° C., diluted with water, treated with solid $NaHCO_3$ and extracted with diethyl ether. The ether extracts were combined, dried ($Na_2SO_4$), filtered and treated with HCl gas. The precipitate was filtered and washed with diethyl ether to afford 1.4 g of the title compound of this preparation. mp 149°–151° C. ¹H NMR (CDCl₃): δ 5.27 (2H, s), 5.42 (2H, s), 7.32–7.39 (5H, m), 8.35 (1H, d, J=6), 8.91 (1H, d, J=6), 9.28 (1H, s).

Preparation 40

4-Methyl-3-pyridinecarboxylic Acid Benzyl Ester

4-Methyl-3-pyridinecarboxylic acid (for preparation, see Schmitz et al., Arch. Pharm. (Weinheim), 1975, 308, 433; 3.0 g, 0.022 mol) was slurried in DMF (N,N-dimethylformamide, 25 ml) and triethylamine (7.60 ml, 0.055 mol). The reaction mixture was treated with benzyl bromide (3.2 ml, 0.026 mol) and stirred at room temperature for two hours. The reaction mixture was poured into 500 ml of ice-water and extracted with diethyl ether (3×200 ml). The organic layers were combined, washed with water (2×100 ml), dried ($Na_2SO_4$), filtered and the solvent was removed in vacuo to afford 4.3 g of an orange oil. The oil was purified via flash chromatography on silica gel (ethyl acetate:hexane: 1:1) to afford 2.4 g of the title compound of this preparation as an oil. ¹H NMR (CDCl₃): δ 2.58 (3H, s), 5.33 (2H, s), 7.12 (1H, d, J=5), 7.31–7.45 (5H, m), 8.50 (1H, d, J=5), 9.09 (1H, s). MS (m/e): 227 (M⁺).

Preparations 41–42

Using substantially the same procedure as recited in Preparation 40, but substituting the appropriate compound for 4-methyl-3-pyridinecarboxylic acid, the following compounds were prepared.

41. 2-Bromo-4-methyl-3-pyridinecarboxylic Acid Benzyl Ester

Prepared from 2-bromo-4-methyl-3-pyridinecarboxylic acid (Baldwin et al., Journal of Organic Chemistry, 1978, 43, 2529). ¹H NMR (CDCl₃): δ 2.26 (3H, s), 5.38 (2H, s), 7.08 (1H, d, J=5), 7.35–7.44 (5H, m), 8.22 (1H, d, J=5).

42. 6-Chloro-2-pyridinecarboxylic Acid 1-Oxide Benzyl Ester

Prepared from the title compound of Preparation 9 hereinabove. ¹H NMR (CDCl₃): δ 5.41 (2H, s), 7.09–7.52 (8H, m).

Preparation 43

2-((5-(2-Ethoxy-2-oxoethyl)-4-methyl-2-thiazolyl)thio)-4-methyl-3-pyridinecarboxylic Acid Benzyl Ester Using substantially the same procedure as recited in Example 1 hereinbove, but substituting the title compound of Preparation 35 for the title compound of Preparation 23, the title compound of this preparation was prepared. ¹H NMR (CDCl₃): δ 1.25 (3H, t, J=7), 2.34 (3H, s), 2.36 (3H, s), 3.71 (2H, s), 4.16 (2H, q, J=7), 5.39 (2H, s), 6.96 (1H, d, J=5), 7.34–7.46 (5H, m), 8.33 (1H, d, J=5). MS (m/e): 442 (M⁺), 217, 144, 91.

Preparation 44

2-((5-(2-Ethoxy-2-oxoethyl)-4-methyl-2-thiazolyl)thio)-6-pyridinecarboxylic Acid Benzyl Ester Using substantially the same procedure as recited in Example 1 hereinabove, but substituting the title compound of Preparation 36 for the title compound of Preparation 23, the title compound of this preparation was prepared. ¹H NMR (CDCl₃): δ 1.24 (3H, t, J=7), 2.36 (3H, s), 3.65 (2H, s), 4.15 (2H, q, J=7), 5.40 (2H, s), 7.23–7.86 (8H, m).

We claim:

1. A compound of the formula

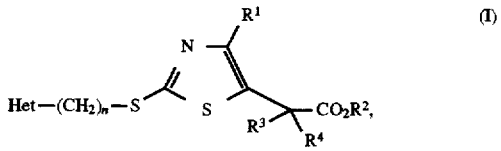

or a pharmaceutically acceptable salt thereof, wherein:

R¹ is H or —(C₁–C₄)alkyl;

R² is H, —(C₁–C₄)alkyl, —(C₃–C₇)cycloalkyl or benzyl;

R³ and R⁴ are taken separately and are independently H or —(C₁–C₄)alkyl, or R³ and R⁴ are taken together to form a five- or six-membered carbocycle;

n is 0, 1 or 2;

Het is

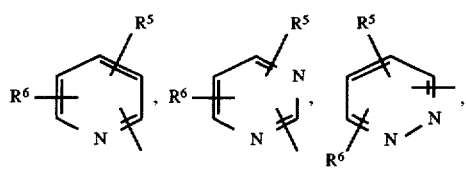

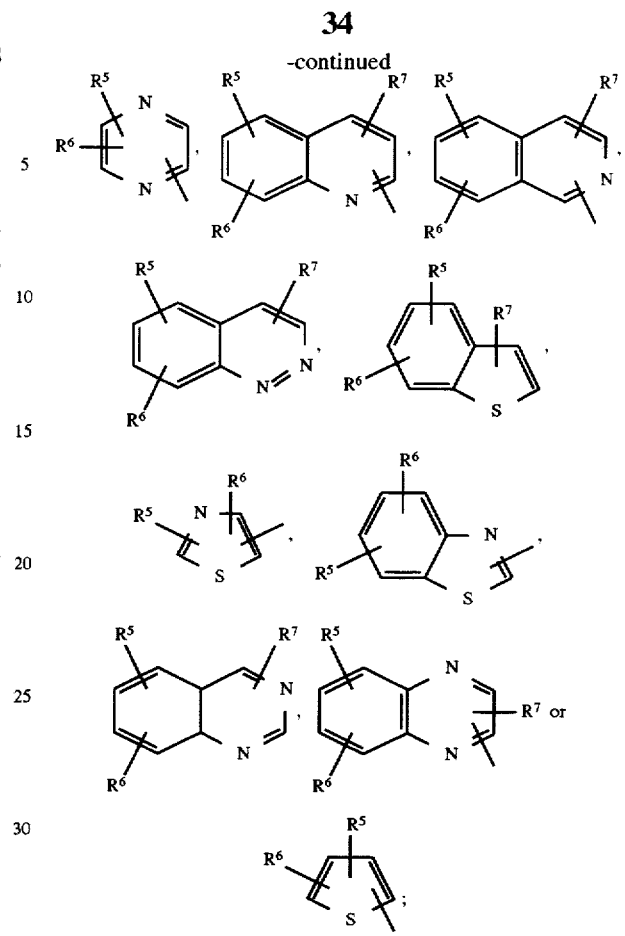

R⁵ is H, methyl, —CF₃, —CHF₂, —CH₂F, chloro, fluoro, bromo, nitro, hydroxy, —(C₁–C₄)alkoxy, mercapto, —(C₁–C₄)alkylthio, —(CH₂)ₚCO₂R⁸, amino, —(C₁–C₄)alkylamino or (C₁–C₄)dialkylamino;

R⁶ and R⁷ are independently H, methyl, —CF₃, —CH₂F, —CHF₂, chloro, fluoro, bromo, nitro, hydroxy, —(C₁–C₄)alkoxy, mercapto, —(C₁–C₄)alkylthio, amino, —(C₁–C₄)alkylamino or —(C₁–C₄)dialkylamino;

R⁸ is H, —(C₁–C₄)alkyl, —(C₃–C₇)cycloalkyl or benzyl; and p is 0, 1 or 2;

provided that when n is 0 and R³ and R⁴ are H, Het is not

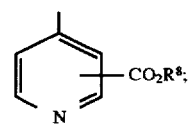

and further provided that when Het is

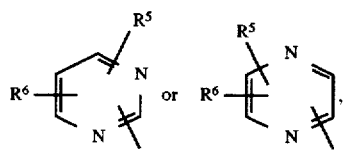

R⁵ and R⁶ are each not chloro, fluoro or bromo.

2. A compound according to claim 1 wherein R³, R⁴ and R⁷ are each H; R² is H, methyl or ethyl; n is 0; Het is

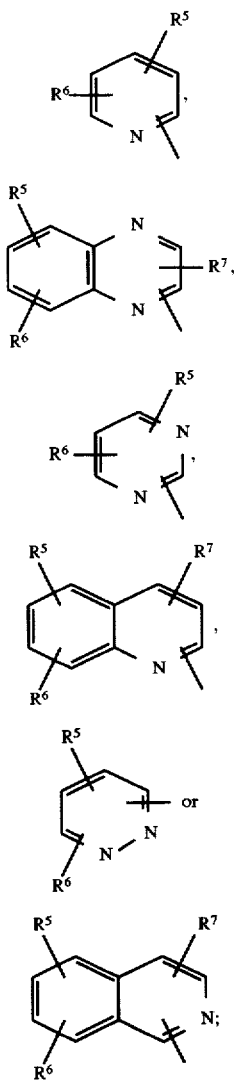

and R⁵ is H, —CO₂R⁸, methyl, —CH₂CO₂R⁸, —(C₁–C₄)alkylthio, methoxy or trifluoromethyl.

3. A compound according to claim 2 wherein Het is

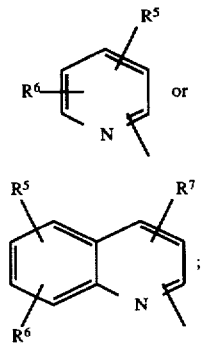

R⁵ is CO₂R⁸; and R⁶ is H, methyl or methoxy.

4. A compound according to claim 3 wherein R⁸ is H.

5. The compound according to claim 4 wherein said compound is 4-((5-carboxymethyl-4-methyl-2-thiazolyl)thio)-8-methoxyquinoline-2-carboxylic acid.

6. The compound according to claim 4 wherein said compound is 2-((5-ethoxy-2-oxoethyl)-4-methyl-2-thiazolyl)thio)-4-methyl-3-pyridinecarboxylic acid.

7. A compound according to claim 3 wherein R⁸ is ethyl.

8. The compound according to claim 7 wherein said compound is 2-((5-carboxymethyl-4-methyl-2-thiazolyl)thio)-6-pyridinecarboxylic acid ethyl ester.

9. A compound according to claim 1 wherein n is 1; Het is

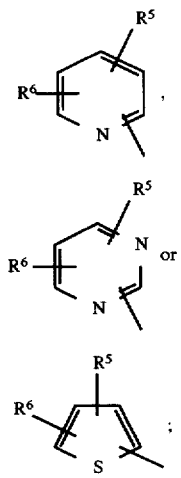

and R⁵ is —CO₂R⁸, —OH or —(C₁–C₄)alkyl.

10. A compound of the formula

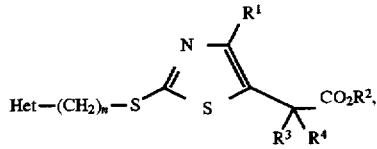

(III)

wherein

R¹ is H or —(C₁–C₄)alkyl;

R² is H, —(C₁–C₄)alkyl, —(C₃–C₇)cycloalkyl or benzyl;

R³ and R⁴ are taken separately and are independently H or —(C₁–C₄)alkyl, or R³ and R⁴ are taken together to form a five- or six-membered carbocycle;

n is 0, 1 or 2;

Het is

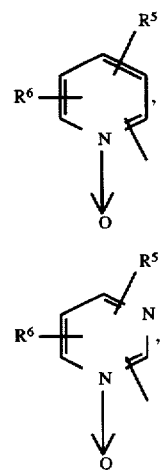

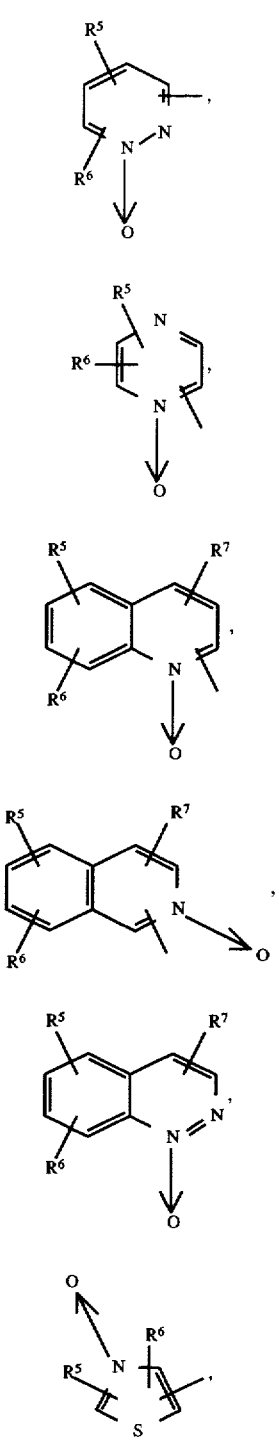

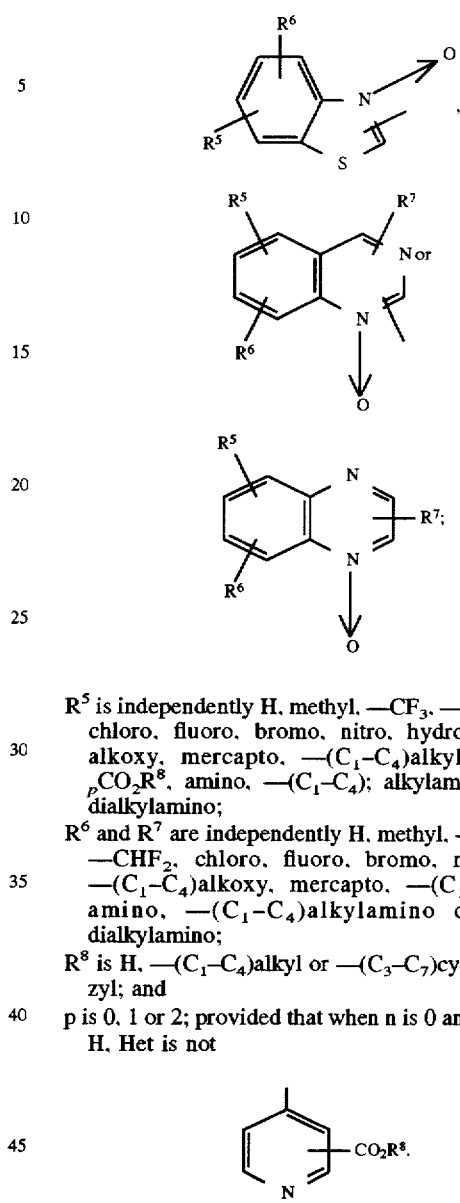

$R^5$ is independently H, methyl, —$CF_3$, —$CHF_2$, —$CH_2F$, chloro, fluoro, bromo, nitro, hydroxy, —$(C_1-C_4)$ alkoxy, mercapto, —$(C_1-C_4)$alkylthio, —$(CH_2)_p CO_2R^8$, amino, —$(C_1-C_4)$ alkylamino or $(C_1-C_4)$ dialkylamino;

$R^6$ and $R^7$ are independently H, methyl, —$CF_3$, —$CH_2F$, —$CHF_2$, chloro, fluoro, bromo, nitro, hydroxy, —$(C_1-C_4)$alkoxy, mercapto, —$(C_1-C_4)$alkylthio, amino, —$(C_1-C_4)$alkylamino or —$(C_1-C_4)$ dialkylamino;

$R^8$ is H, —$(C_1-C_4)$alkyl or —$(C_3-C_7)$cycloalkyl or benzyl; and p is 0, 1 or 2; provided that when n is 0 and $R^3$ and $R^4$ are H, Het is not 11. A method for treating a viral infection in a mammal comprising administering to said mammal an effective amount of a compound according to claim 1 or a pharmaceutical composition thereof.

12. A pharmaceutical composition for use in a mammal suffering from a viral infection which comprises an effective amount of a compound according to claim 1 and a pharmaceutically acceptable carrier or diluent.

* * * * *